US011642021B2

(12) United States Patent
Tsai et al.

(10) Patent No.: US 11,642,021 B2
(45) Date of Patent: May 9, 2023

(54) MONITORING NEUROLOGICAL FUNCTIONAL STATUS

(71) Applicant: MUSC Foundation for Research Development, Charleston, SC (US)

(72) Inventors: Nancey Trevanian Tsai, Hanahan, SC (US); Mark Evald Semler, Mount Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 668 days.

(21) Appl. No.: 16/569,940

(22) Filed: Sep. 13, 2019

(65) Prior Publication Data

US 2020/0000334 A1    Jan. 2, 2020

Related U.S. Application Data

(63) Continuation of application No. 14/787,564, filed as application No. PCT/US2014/036349 on May 1, 2014, now Pat. No. 10,448,825.

(Continued)

(51) Int. Cl.
*A61B 3/00* (2006.01)
*A61B 5/00* (2006.01)
(Continued)

(52) U.S. Cl.
CPC ............ *A61B 3/113* (2013.01); *A61B 3/0025* (2013.01); *A61B 3/0033* (2013.01);
(Continued)

(58) Field of Classification Search
CPC ........ A61B 3/00–185; A61B 5/16–168; A61B 5/18; A61B 5/4058; A61B 5/4064;
(Continued)

(56) References Cited

U.S. PATENT DOCUMENTS 4,815,839 A    3/1989 Waldorf
4,850,691 A    7/1989 Gardner
(Continued)

FOREIGN PATENT DOCUMENTS

EP    1726260    11/2006
JP    S62275432 A    11/1987
(Continued)

OTHER PUBLICATIONS

Buonaguidi et al., "Blink Reflexes in Severe Traumatic Coma", Journal of Neurology, Neurosurgery, and Psychiatry, 1979,42,470-474.
(Continued)

*Primary Examiner* — David J. McCrosky
(74) *Attorney, Agent, or Firm* — Riverside Law LLP

(57) ABSTRACT

A device for measuring eye movement in a human subject comprises a housing, at least one stimulator mounted to the housing, and a sensor. The at least one stimulator is configured to provide stimulus to one or both eyes of the subject. The sensor is configured to collect information related to movement of one or both eyes of the subject. The device also includes a user interface that is configured to control the at least one stimulator and display information collected by the camera.

32 Claims, 21 Drawing Sheets

Related U.S. Application Data

(60) Provisional application No. 61/818,087, filed on May 1, 2013.

(51) Int. Cl.
*A61B 3/113* (2006.01)
*A61B 5/11* (2006.01)
*A61B 5/398* (2021.01)
*A61B 3/11* (2006.01)
*A61B 3/14* (2006.01)
*A61B 5/16* (2006.01)

(52) U.S. Cl.
CPC ............ *A61B 3/0041* (2013.01); *A61B 3/112* (2013.01); *A61B 3/145* (2013.01); *A61B 5/0059* (2013.01); *A61B 5/0077* (2013.01); *A61B 5/1103* (2013.01); *A61B 5/398* (2021.01); *A61B 5/4094* (2013.01); *A61B 5/0013* (2013.01); *A61B 5/0022* (2013.01); *A61B 5/162* (2013.01); *A61B 5/4863* (2013.01); *A61B 2560/0406* (2013.01)

(58) Field of Classification Search
CPC ... A61B 5/4076; A61B 5/4082; A61B 5/4088; A61B 5/4094
See application file for complete search history.

(56) References Cited

U.S. PATENT DOCUMENTS

| | | | |
|---|---|---|---|
| 5,137,345 A | 8/1992 | Waldorf | |
| 5,333,009 A | 7/1994 | Gell, Jr. | |
| 5,570,698 A | 11/1996 | Liang | |
| 5,786,765 A | 7/1998 | Kumakura | |
| 5,867,587 A | 2/1999 | Aboutalib | |
| 6,091,334 A | 7/2000 | Galiana | |
| 6,542,081 B2 | 4/2003 | Torch | |
| 6,572,562 B2 | 6/2003 | Marshall | |
| 6,717,518 B1 | 4/2004 | Pirim | |
| 6,887,199 B2 | 5/2005 | Bridger | |
| 7,011,410 B2 | 3/2006 | Bolger | |
| 7,043,056 B2 | 5/2006 | Edwards | |
| 7,216,978 B2 * | 5/2007 | Perez | A61B 3/145 351/159.74 |
| 7,344,251 B2 | 3/2008 | Marshall | |
| 7,347,551 B2 | 3/2008 | Fergason | |
| 7,401,920 B1 | 7/2008 | Kranz | |
| 7,438,418 B2 | 10/2008 | Marshall | |
| 7,488,294 B2 | 2/2009 | Torch | |
| 7,515,054 B2 | 4/2009 | Torch | |
| 7,553,021 B2 | 6/2009 | Fergason | |
| 7,614,745 B2 | 11/2009 | Waldorf | |
| 7,647,098 B2 | 1/2010 | Prichep | |
| 7,720,530 B2 | 5/2010 | Causevic | |
| 7,771,353 B2 * | 8/2010 | Luce | A61B 3/101 351/200 |
| 7,791,491 B2 | 9/2010 | Johns | |
| 7,810,928 B2 | 10/2010 | Kandel | |
| 7,938,785 B2 | 5/2011 | Aguilar | |
| 7,959,293 B2 | 6/2011 | Huth | |
| 7,963,655 B2 | 6/2011 | Huth | |
| 7,986,991 B2 | 7/2011 | Prichep | |
| 8,025,404 B2 | 9/2011 | Bolger | |
| 8,092,023 B2 | 1/2012 | Korb | |
| 8,096,946 B2 | 1/2012 | Burton | |
| 8,100,534 B2 | 1/2012 | Huth | |
| 8,215,774 B2 | 7/2012 | Korb | |
| 8,306,271 B2 | 11/2012 | Yoda | |
| 8,314,707 B2 | 11/2012 | Kobetski | |
| 8,333,475 B2 | 12/2012 | Sugio | |
| 8,356,899 B2 | 1/2013 | Hirata | |
| 8,379,918 B2 | 2/2013 | Pfleger | |
| 8,388,136 B2 | 3/2013 | Huth | |
| 8,391,967 B2 | 3/2013 | Freer | |
| 8,393,734 B2 | 3/2013 | Privitera | |
| 8,534,840 B2 | 9/2013 | Siminou | |
| 10,478,063 B2 * | 11/2019 | Matsui | G06V 40/19 |
| 2004/0246441 A1 | 12/2004 | Stark | |
| 2005/0007552 A1 | 1/2005 | Fergason | |
| 2005/0165327 A1 | 7/2005 | Thibault | |
| 2007/0237715 A1 * | 10/2007 | Luce | A61B 3/101 351/200 |
| 2007/0273611 A1 | 11/2007 | Torch | |
| 2009/0174701 A1 * | 7/2009 | Cotter | G06T 7/20 348/42 |
| 2011/0077548 A1 * | 3/2011 | Torch | A61B 5/165 600/558 |
| 2011/0170064 A1 | 7/2011 | Taylor | |
| 2011/0176106 A1 | 7/2011 | Lewkowski | |
| 2012/0008091 A1 | 1/2012 | Stewart | |
| 2012/0182149 A1 | 7/2012 | Moreno Valenzuela | |
| 2012/0230547 A1 | 9/2012 | Durnell | |
| 2012/0238831 A1 | 9/2012 | Benford | |
| 2012/0293773 A1 | 11/2012 | Publicover | |
| 2012/0330178 A1 | 12/2012 | Kraft | |
| 2013/0012832 A1 | 1/2013 | Zelinsky | |
| 2014/0152792 A1 | 6/2014 | Krueger | |
| 2016/0073874 A1 | 3/2016 | Tsai | |
| 2016/0317056 A1 | 11/2016 | Moon | |

FOREIGN PATENT DOCUMENTS

| | | |
|---|---|---|
| JP | H4126505 U | 11/1992 |
| JP | 2004126505 | 4/2004 |
| JP | 2004283609 | 10/2004 |
| JP | 2004329879 | 11/2004 |
| JP | 2005278670 | 10/2005 |
| JP | 2007255669 | 10/2007 |
| JP | 2007531579 | 11/2007 |
| WO | 2005094667 | 10/2005 |
| WO | 2012061871 A1 | 5/2012 |
| WO | 2014179558 A1 | 11/2014 |
| WO | 2016023126 A1 | 2/2016 |

OTHER PUBLICATIONS

Esteban et al., "Blink Reflex in Huntington's Chorea and Parkinson's Disease", Acta Neurologica Scandinavica, Aug. 1975, 52(2), 145-157.

Extended European Search Report for App. No. EP18802270.1, dated Nov. 19, 2020, 8 pages.

Konrad et al., "Catecholamine Functioning in Children with Traumatic Brain Injuries and Children with Attention-Deficit/Hyperactivity Disorder", Cognitive Brain Research, May 2003, 16(3), 425-433.

Notice of Allowance dated Jun. 17, 2019 for U.S. Appl. No. 14/787,564 (pp. 1-14).

Office Action (Final Rejection) dated Apr. 25, 2022 for U.S. Appl. No. 16/613,522 (pp. 1-7).

Office Action dated Nov. 10, 2021 for U.S. Appl. No. 16/613,522 (pp. 1-10).

Office Action dated Nov. 14, 2018 for U.S. Appl. No. 14/787,564 (pp. 1-10).

Saunders et al., "Loss of Emotional Experience After Traumatic Brain Injury: Findings With the Startle Probe Procedure", Neuropsychology, 2006, 20(2), 224-231.

* cited by examiner

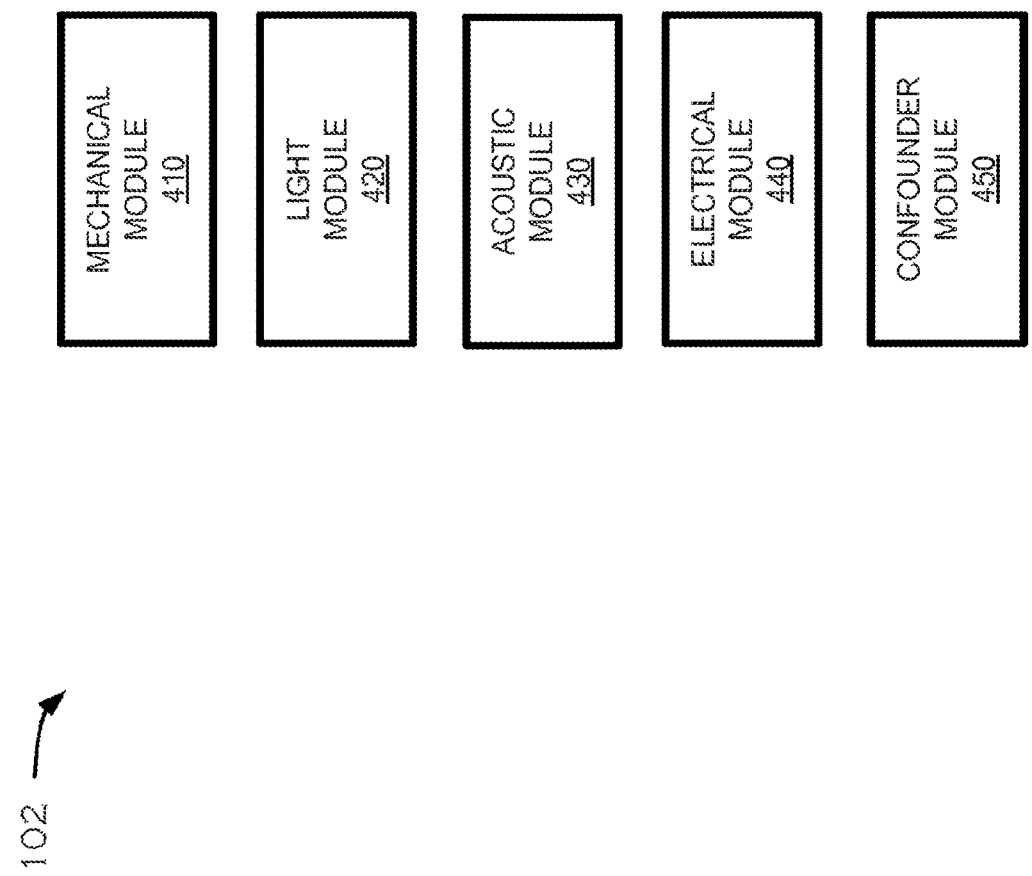

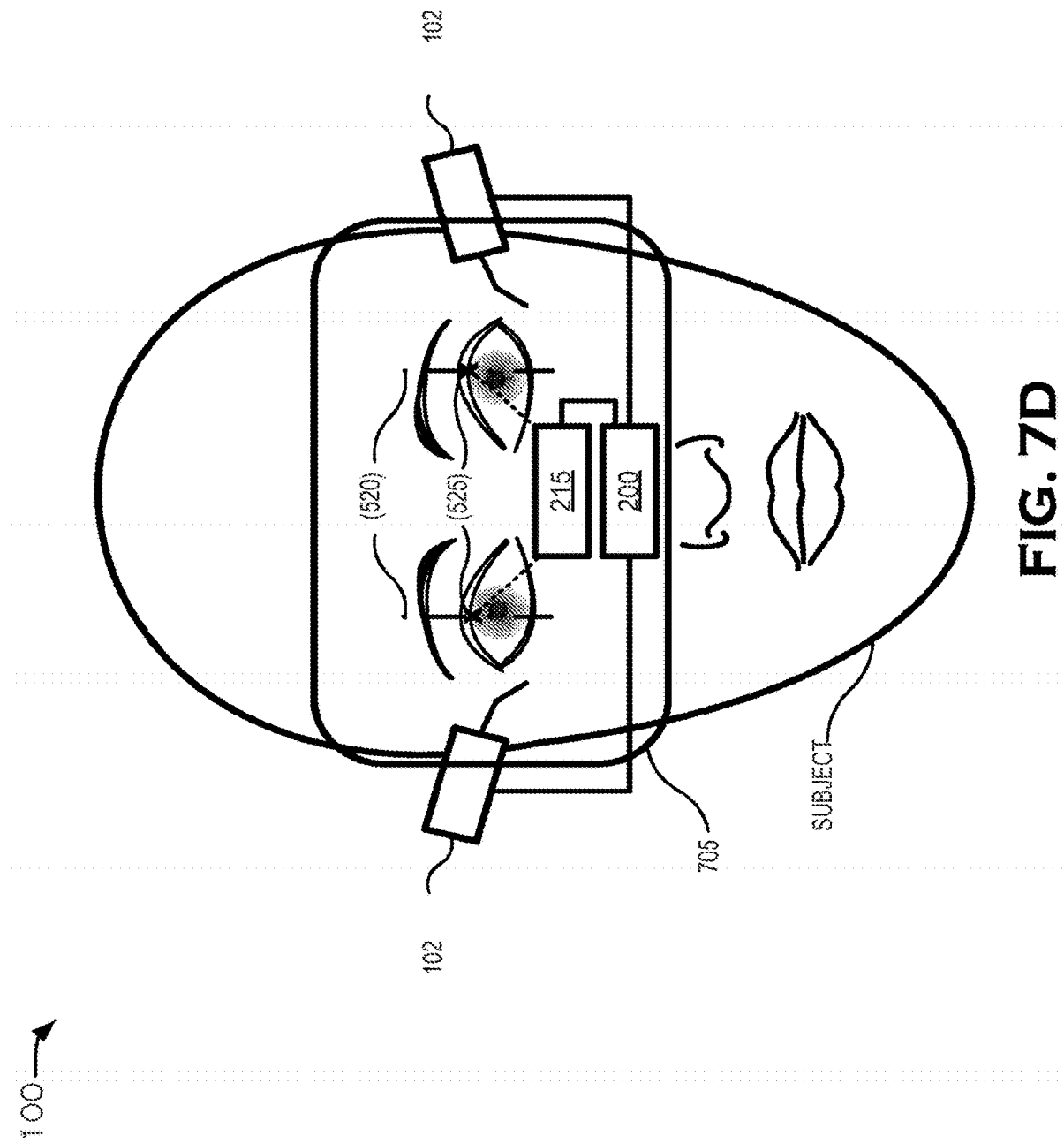

| NO IMPAIRMENT 1210 | SOME IMPAIRMENT 1215 | SIGNIFICANT IMPAIRMENT 1220 |
|---|---|---|
| $\Delta B0 < br1$ | $br1 \leq \Delta B0 < br2$ | $br2 \leq \Delta B0$ |
| $\Delta B1 < nbr1$ | $nbr1 \leq \Delta B1 < nbr2$ | $nbr2 \leq \Delta B1$ |
| $\Delta R1 < c1$ | $c1 \leq \Delta R1 < c2$ | $c2 \leq \Delta R1$ |
| $\Delta L1 < c1$ | $c1 \leq \Delta L1 < c2$ | $c2 \leq \Delta L1$ |
| $\Delta R2 < nc1$ | $nc1 \leq \Delta R2 < nc2$ | $nc2 \leq \Delta R2$ |
| $\Delta L2 < nc1$ | $nc1 \leq \Delta L2 < nc2$ | $nc2 \leq \Delta L2$ |
| $\Delta LR1 < dr1$ | $dr1 \leq \Delta LR1 < dr2$ | $dr2 \leq \Delta LR1$ |
| $\Delta LR2 < ndr1$ | $ndr1 \leq \Delta LR2 < ndr2$ | $ndr2 \leq \Delta LR2$ |
| ... | | ... |

FIG. 12

MONITORING NEUROLOGICAL FUNCTIONAL STATUS

REFERENCE TO RELATED APPLICATION

This application is a continuation of U.S. patent application Ser. No. 14/787,564, filed on Oct. 28, 2015, which is a national stage filing of International Application No. PCT/US2014/036349 filed on May 1, 2014, which claims priority to U.S. Provisional Patent Application No. 61/818,087, filed May 1, 2013, each of which are incorporated herein by reference in their entireties.

BACKGROUND

Mild traumatic brain injury (mTBI), sometimes referred to as a concussion, mild brain injury, mild head injury (MHI), or minor head trauma, is the most common type of traumatic brain injury. The rate at which mTBI occurs is not accurately known, which may be due to the subjective nature of its detection and diagnosis, and the possibility that occurrences of mTBI are being under-reported. Some estimates suggest that mTBI occurs in more than six (6) per one thousand (1,000) people per year. Common causes of concussions are sports injuries, bicycle accidents, car accidents and falls. Concussions caused by sports injuries and bicycle injuries most commonly occur in children and young adults, and those caused by car accidents and falls most commonly occur in adults and the elderly.

Part of the problem of the diagnosis of mTBI is that there are little differences between the diagnostic criteria and the manifest symptoms. mTBI implies decreased cognitive function and denotes change in personality and behaviors that are uncharacteristic of the person who has sustained an mTBI. While there are known systems and methods for identifying or measuring cognitive function in a subject, there are currently no devices and methods that objectively measure, on a near real-time basis in the field (e.g., the playing field, battlefield, site of an automobile accident, etc.), the likelihood of altered brain reflexes and/or physiology associated with a neurological condition within a subject.

SUMMARY

A device for measuring a reflex reaction in a subject suspected of suffering from mTBI is disclosed. In particular, the device measures a reflex reaction in a subject that has suffered an injury and compares that reaction to a baseline reaction in the same subject taken prior to suffering the injury.

In one embodiment reflexive eye movement is tracked. The device for measuring such movement comprises a housing, at least one stimulator mounted to the housing, and a tracking sensor that measures the eye movement, such as a camera. The at least one stimulator is configured to provide stimulus to one or both eyes of the subject producing the desired reaction. The tracking device, in this example a camera, is configured to collect information related to movement of one or both eyes of the subject. The device also includes a user interface that is configured to control the at least one stimulator and display information collected by the camera.

In another embodiment, a device for measuring blink reflex in a human subject comprises a camera configured to track movement of one or both eyelids of the subject, a stimulator configured to provide stimulus to one or both eyelids of the subject, and one or more processors. The one or more processors execute instructions to track the movement of the one or more eyelids using the camera, stimulate the subject using the stimulator to provoke a first blink reflex, the first blink reflex corresponding to an involuntary blink, of the one or more eyelids, determine, based on information received from the camera, a first time period being associated with the first blink reflex, calculate and absolute difference between the first time period and a second time period, the second time period being associated with a second blink reflex of the subject, the second blink reflex measured when the subject was known not to be suffering from a neurological condition, determine, based on obtaining the second information, whether the subject is potentially suffering from a neurological condition based on a difference between the first time period and the second time period relative to a threshold, and provide an indication that the subject is suffering from a neurological condition when the difference between the first time period and the second time period, is greater than the threshold.

In yet another embodiment, a method for measuring a blink reflex of a subject using a blink reflex device comprises stimulating one or both eyes of the subject using at least one stimulator so as to cause an involuntarily blink response in the subject, measuring a time period from the stimulating step to when one or both eyes initiates the involuntary blink response, and displaying information that identifies the time period.

BRIEF DESCRIPTION OF THE DRAWINGS

FIG. 5 is a diagram of an example modules that may be associated with a stimulator component of FIG. 1A-1D;

FIGS. 7A-7D are diagrams of example blink reflex devices associated with different stimulator modules;

FIG. 12 is a diagram of an example data structure that stores information associated with a change in blink reflex of a subject.

DETAILED DESCRIPTION

The devices and methods described herein may be used to determine whether a human subject suffers from impaired neurological function based on a change in a blink reflex, blink period, or other brain reflex of the subject. Impaired neurological function may result from a brain injury, such as mTBI, SIS, impaired neurological function (e.g., due to fatigue, exhaustion, a developmental abnormality, an illness other than a neurological illness, etc.) and/or a degenerative neurological condition such as Alzheimer's disease and Parkinson's disease (hereinafter collectively referred to as a "neurological condition"). In the event that it is determined that the subject may suffer from a neurological condition, the devices and methods may enable a level of severity of such a neurological condition.

Figure 1A:
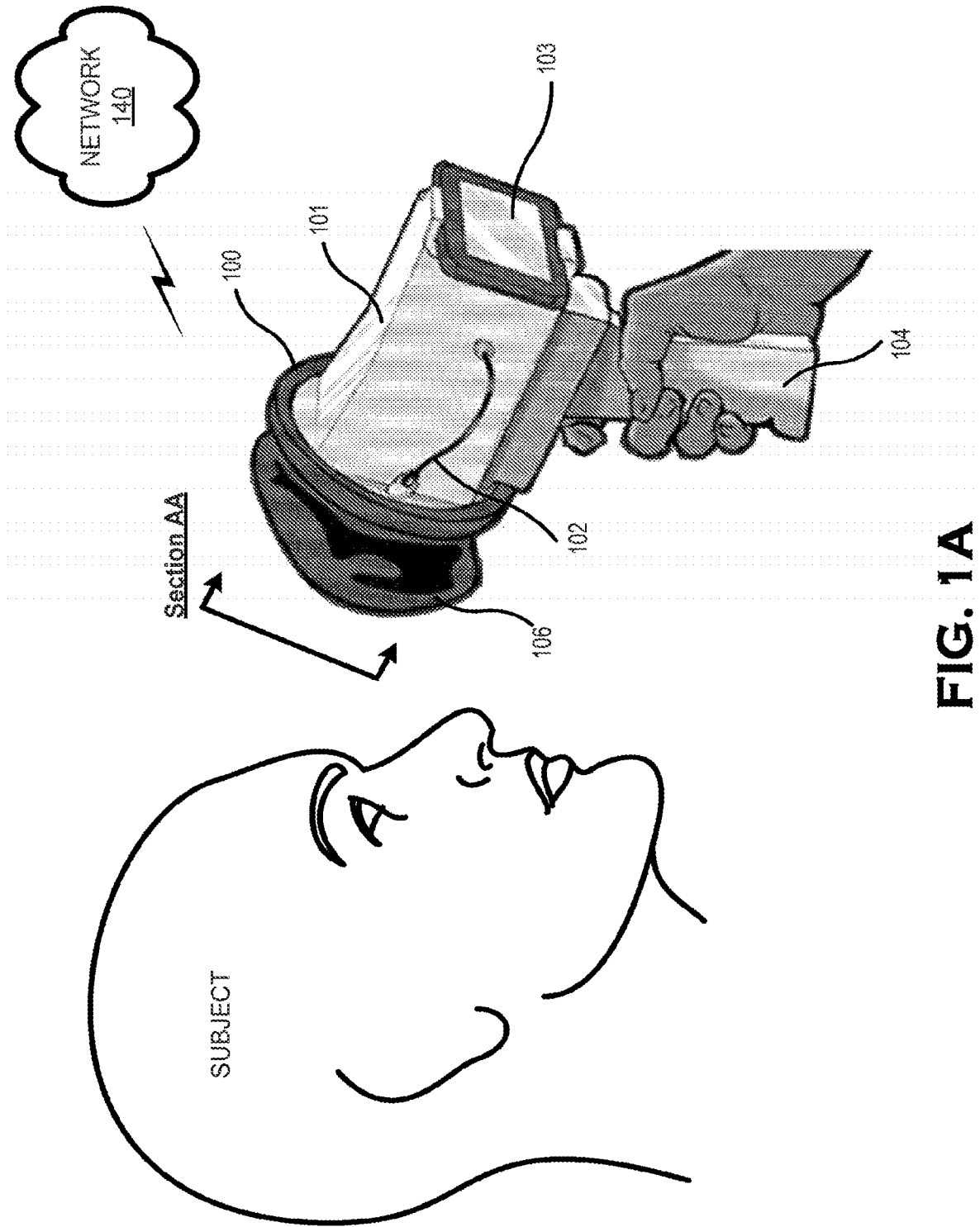
FIGS. 1A-1D are diagrams of an example embodiment of the blink reflex device.
Figure 1B:
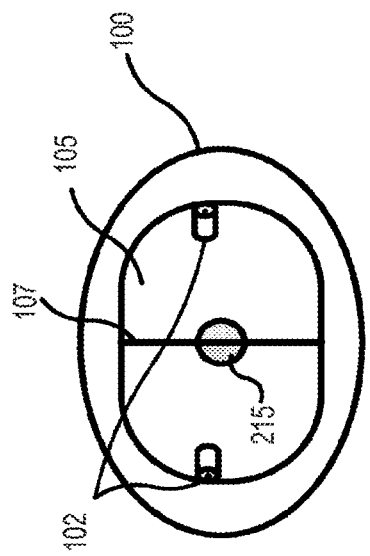
Figure 1C:
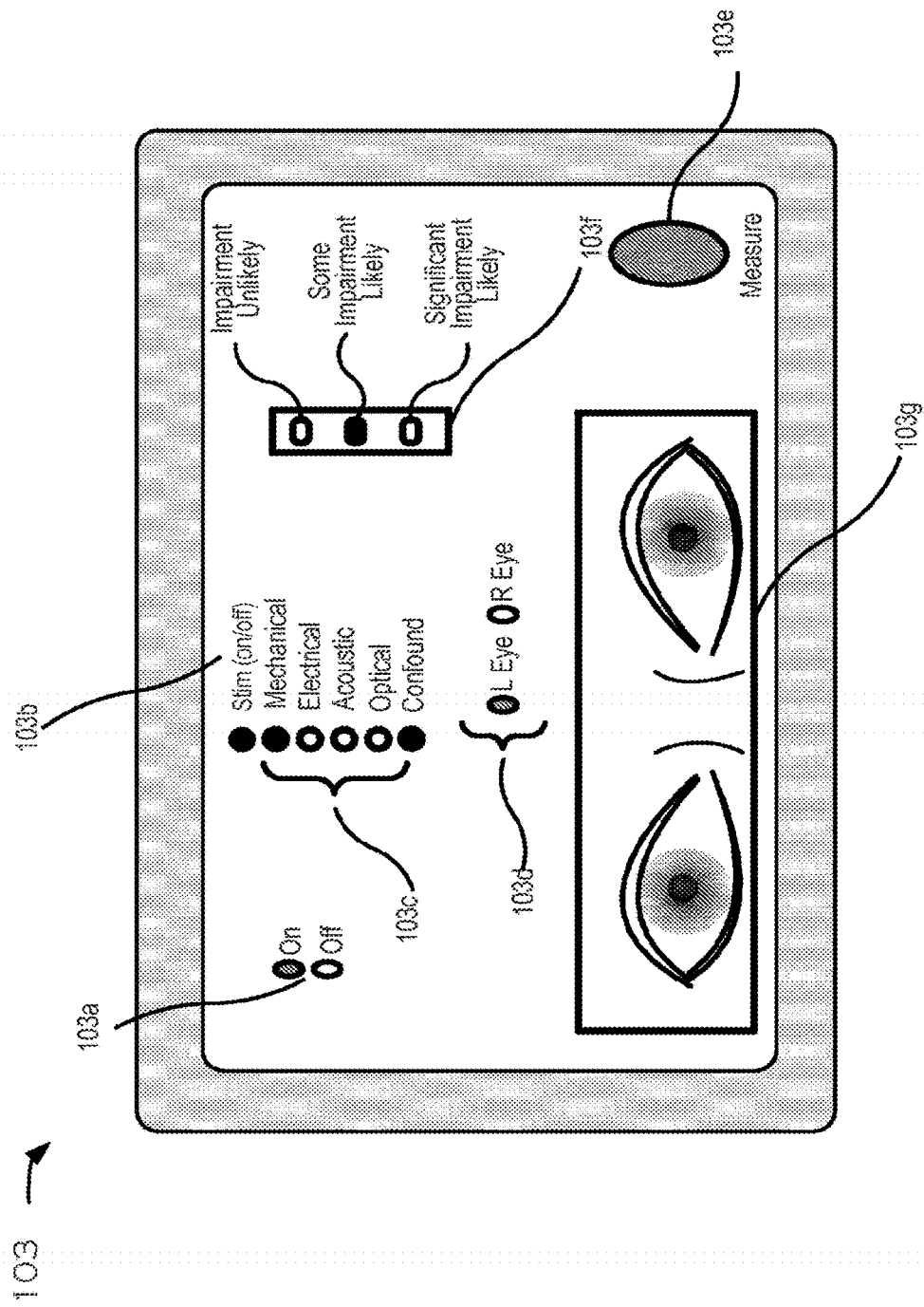

FIGS. 1A-1D are diagrams of an example blink reflex device 100. As shown in FIG. 1A, blink reflex device 100 may include a housing 101, a stimulator 102, and a sensor 215 (shown in FIG. 1B), such as a camera. With reference to FIG. 2, blink reflex device 100 may communicate with server 120 and/or database 130 via network 140. Blink reflex device 100 may include a collection of components such as, for example, a user interface 103, a handle 104, and a screen 105 (shown in FIG. 1B).

Device 100 may include a flexible material 106 attached to the housing 101 configured to fit against the face, head, or neck of the subject. Flexible material 106, together with housing 101, defines a cavity within which the stimulators 102, sensor 215, and screen 105 are disposed. Flexible material 106 conforms to the shape and contours of the subject so as to create a temporary seal between the subject and blink reflex device 100. The seal may enable stimulator 102 and or sensor 215 (shown in FIG. 1B) to operate with minimal external stimulation or light. Screen 105 may also, or alternatively, minimize the likelihood that the subject is distracted by objects or activities that are outside the cavity. Handle 104 may include a rigid material that is part of or connect to housing 101 configured to be held by an operator of the blink reflex device 100. User interface 103 allows the operator to operate and/or control blink reflex device 100.

Figure 1D:
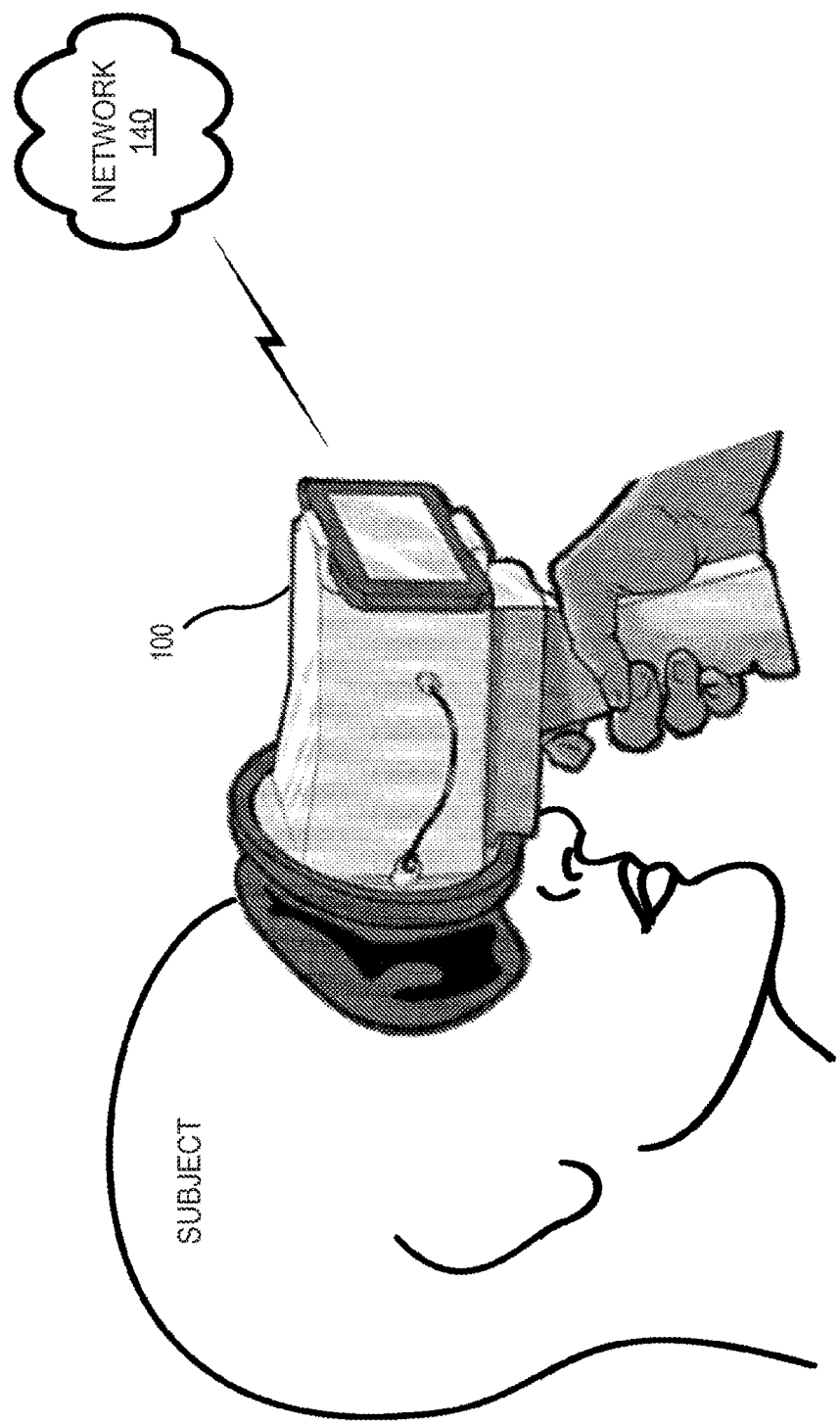
Figure 2:
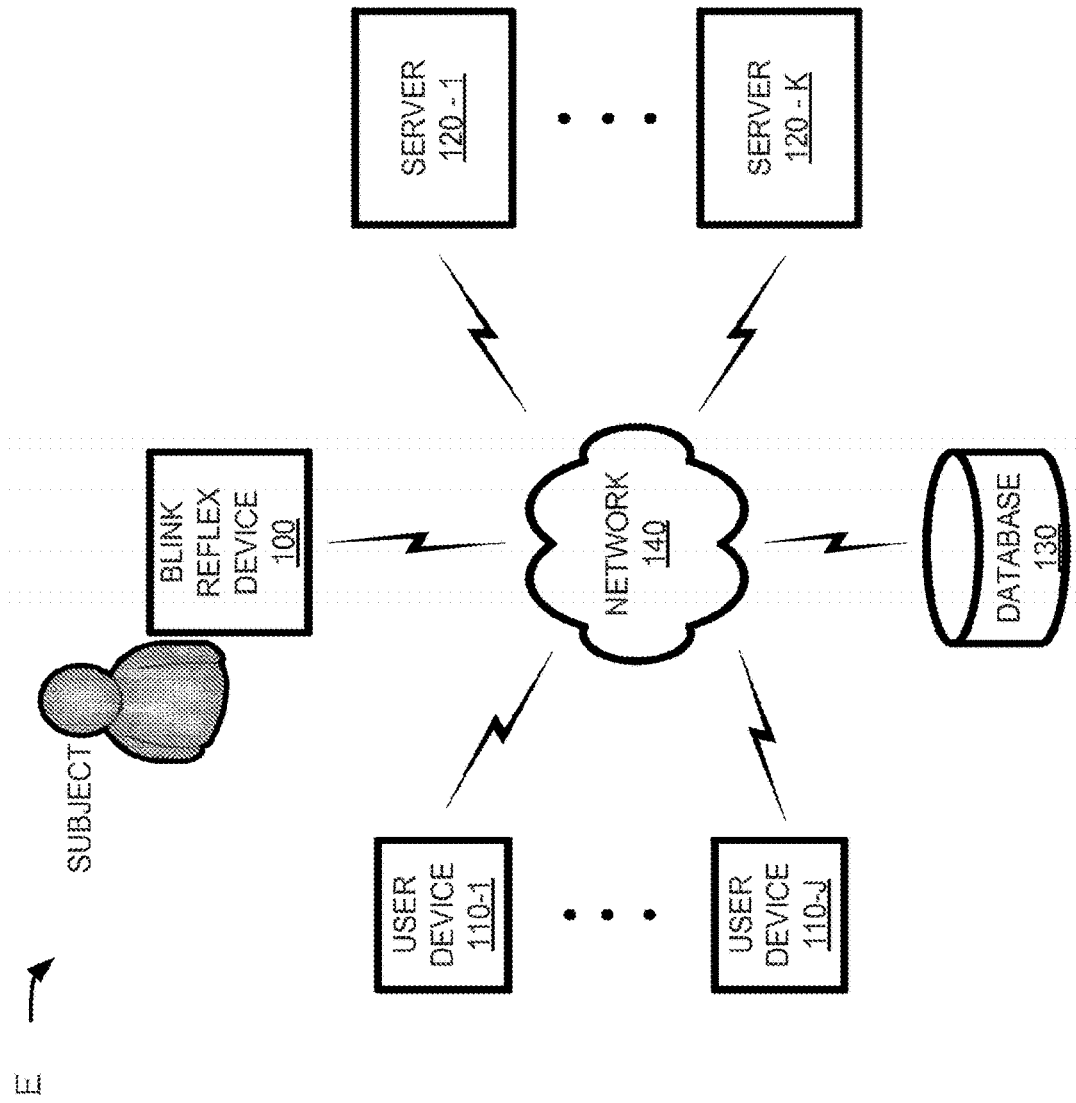
FIG. 2 is a diagram of an example environment in which the blink reflex device shown in FIGS. 1A-1D may be implemented.

By way of example, an operator, of blink reflex device 100, may place blink reflex device 100 against the subject's face to detect and monitor one or both eyes of the subject to measure and/or obtain information associated with a blink reflex and/or blink period of the subject (e.g., as shown in FIG. 1D). FIG. 1B, which depicts section AA of blink reflex device 100 as shown in FIG. 1A, depicts a pair of stimulators 102, sensor 215, screen 105, and a divider 107. Stimulators 102 provide mechanical stimuli (e.g., a puff of fluid, etc.) and/or some other type of stimuli (e.g., light, acoustic, electrical, etc.) to the subject. Sensor 215 measures the blink reflex and/or blink period of the subject. Sensor 215 may also, or alternatively, measure eye movement and/or pupillary response of the subject. Sensor 215 may also use facial recognition to identify a subject.

Figure 3:
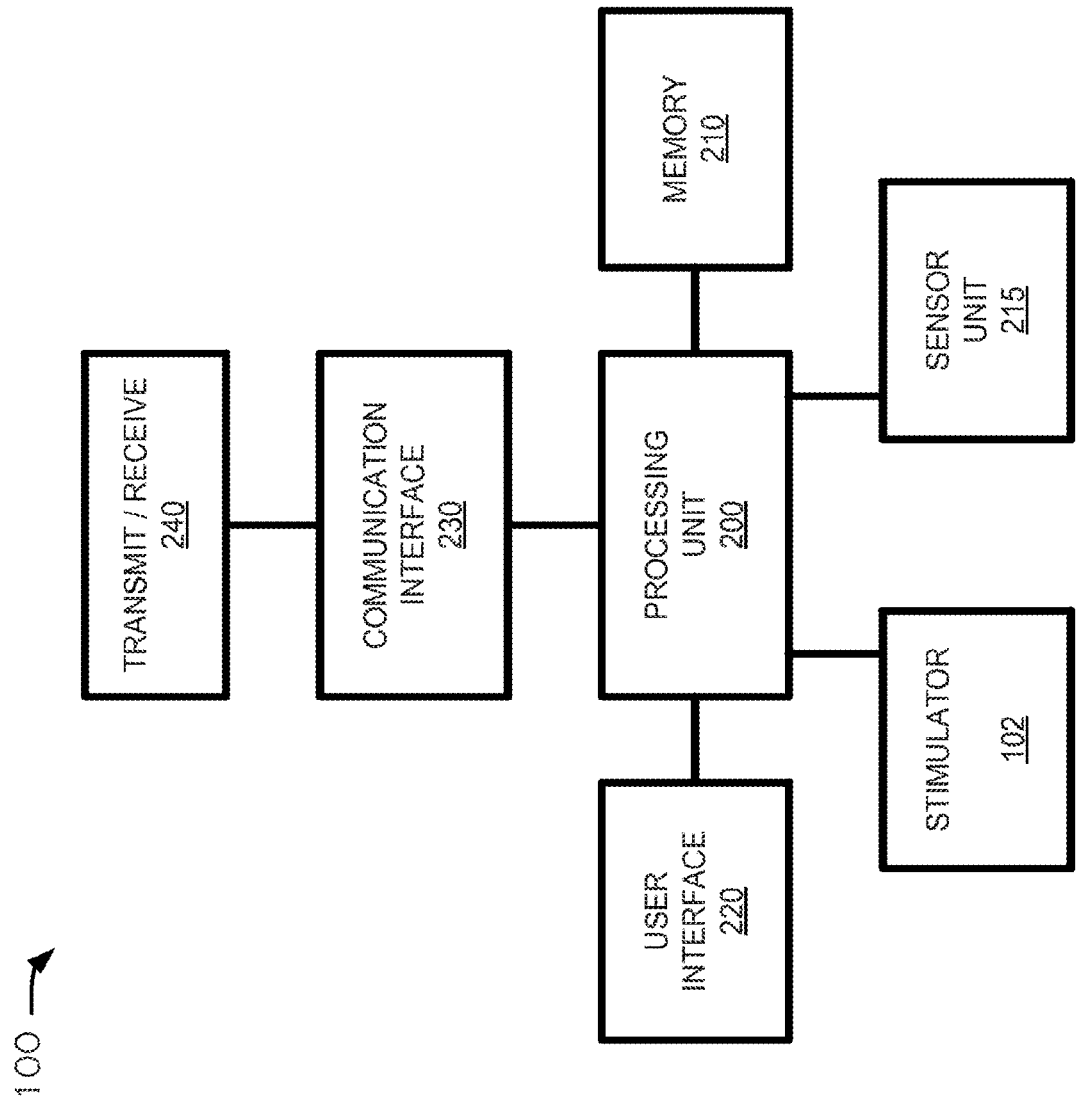
FIG. 3 is a diagram of example components of a blink reflex device of FIG. 1A-1D.

Stimulator 102 may include one or more components to provide mechanical, electrical, optical, and/or acoustic stimulation to a subject, to trigger a blink reflex in the subject. The stimulation may excite certain neural pathways in the brain and/or nervous system of the subject, which may trigger the blink reflex. For example, optical stimulation (e.g., due to a beam of bright light to the eye of the subject) may stimulate the superior colliculus structure and/or some other structure in the brain to cause the subject to involuntarily blink. Additionally, or alternatively, mechanical stimulation (e.g., a puff of air to the eye, a pin prick or tap to the proximity of the eye, etc.) and/or electrical stimulation may excite the corneal reflex and/or some neurological structure of the subject causing the subject to involuntarily blink. Additionally, or alternatively, acoustic stimulation (e.g., a sudden loud tone, noise, music, etc.) may stimulate the inferior colliculus structure and/or some other structure in the brain to cause the subject to involuntarily blink or elicit some other brain reflex. Stimulator 102 may output the stimulation based on an instruction received from processing unit 200 (shown in FIG. 3) and/or a user of blink reflex device 100. Stimulator 102 may also, or alternatively, include a device to confound or distract the subject to attenuate a tendency by the subject to anticipate certain stimuli, which may affect the integrity of the blink reflex data and/or other brain reflex data.

With reference to FIG. 5, example modules that may be associated with a stimulator 102 are shown. Stimulator 102 may include a mechanical module 410, a light module 420, an acoustic module 430, an electrical module 440 and/or a confounder module 450. Although FIG. 5 shows example modules of stimulator 102, additionally, or alternatively, stimulator 102 may include fewer modules, additional modules, different modules, or differently arranged modules than depicted in FIG. 5. Additionally, or alternatively, one or more modules of stimulator 102 may perform one or more tasks described as being performed by one or more other modules of stimulator 102.

Divider 107 forms a barrier between a right side and left side of the cavity defined by the flexible material preclude stimulus, provided by one of the stimulators 102, from inadvertently stimulating the eye that is closest to the other stimulator 102. Divider 107 is configured such that sensor 215 can measure the blink reflex, blink period, eye movement, or pupillary response of one or both eyes of the subject. Divider 107 may be made of a flexible material that conforms to the shape of the subjects face, nose, forehead, etc. Divider 107 may also, or alternatively, be removable.

With reference to FIG. 1B, screen 105 may be used to display instructions for the subject during a confounding operation or measurement, a target can be displayed at which the subject is to stare at or track during a measurement, etc. Screen 105 may enable questions, lights, etc. associated with a confounding operation to be displayed for the subject. Screen 105 may provide means of optical stimulus in place of or in combination with stimulus provided by stimulator 102.

As shown in FIG. 1C, user interface 103 may include a collection of buttons, fields and/or indicators, such as a power button 103a, a stimulator button 103b, a stimuli selector button 103c, an eye selector button 103d, a measure button 103e, an indicator 103f, and a subject field 103g. User interface 103 may receive information from processing unit 200 (shown in FIG. 3) and may display the received information. User interface 103 may receive information from an operator of blink reflex device 100 and may provide the entered information to processing unit 200. The number of components, buttons, fields and/or indicators, illustrated in FIG. 1C is provided for explanatory purposes only. In practice, there may be additional components, fields, buttons, and/or indicators; fewer components, fields, buttons, and/or indicators; different components, fields, buttons, and/or indicators; or differently arranged components, fields, buttons, and/or indicators than illustrated in FIG. 1C.

Power button 103a may include one or more buttons that enable blink reflex device 100 to power up or power down. Stimulator button 103b enables the operator to control blink reflex device 100 to provide stimulus to the subject or to preclude stimulus from being provided to the subject.

Stimuli selector button 103c enables selection of a type of stimulus (e.g., mechanical, electrical, acoustic, optical, etc.) to be provided to the subject by blink reflex device 100. Stimuli selector button 103c may also, or alternatively, enable control of whether or not blink reflex device 100 will provide confounding to the subject. Eye selector button 103d may enable selection of the left eye, right eye, or both eyes from which information associated with a blink reflex and/or blink period is to be obtained by blink reflex device 100. Measure button 103e, when selected by the user, causes blink reflex device 100 to measure the blink reflex and/or blink period of the subject in a manner that includes the type of stimuli with or without confounding as selected by the user using stimuli selector button 103c. Indicator 103f may include one or more lights, light emitting diodes, a display, a user interface, speaker, etc. that enables blink reflex device 100 to output an indication, notification, and/or sound that can be viewed or heard by an operator of blink reflex device 100 that identifies whether the subject suffers from a neurological condition and/or a level of severity of such a neurological condition. For example, if blink reflex device 100 determines that the subject likely suffers from some brain injury or degenerative neurological condition that is not significant, blink reflex device 100 may cause a light, indication, notification, etc. to be lighted or displayed in a manner that indicates that the subject suffers from some brain injury or degenerative neurological condition. Subject field 103g may include an image or video of the subject as seen by sensor 215 before, during, and/or after measurements are taken on the subject.

FIG. 1D is a diagram of blink reflex device 100 being used to take a blink reflex and/or blink period measurement from the subject. As shown in FIG. 1D, the operator may place blink reflex device 100 against the face of the subject to obtain information associated with the blink reflex and/or blink period in a manner described above.

Device 100 and its associated methods may enable, for example, a blink reflex device to measure a response associated with an eye blink of a subject (hereinafter the "blink reflex"). The blink reflex (described in greater detail herein) may generally correspond to a time period from when stimulation (described herein) is received by the subject within the proximity of the eye of the subject to when the subject initiates or begins to blink (e.g., when one or more of the subject's eyelids, in an open state, begin to close) in response to the stimulation.

Device 100 and its associated methods may enable a blink reflex device to measure a period of time that it takes for the subject to blink his or her eye (hereinafter, the "blink period"). The blink period may be on the subject's response to stimulation; intentional and voluntary blink; and/or involuntary, unintentional or subconscious blink. The blink period may be measured from when the subject starts to blink (e.g., when the eyelid, in an open state, begins to close) to when the subject stops the blink and the eye of the subject returns to the open state (e.g., when the eyelid, returning from a closed state, stops opening).

Device 100 and its associated methods may also, or alternatively, enable the blink reflex device to detect when the subject exhibits an abnormal blink and may reject, discard, and/or ignore any data associated with a blink reflex measurement of the abnormal blink or other non-reflex closure or movement of the eye. An abnormal blink may occur when the eye of the subject does not fully return to the open state, does not fully close, remains closed for a prolonged time period (e.g., greater than 2 times, 5 times, 10 times, 15 times, etc. of a normal blink period) (sometimes referred to as a "micro-sleep").

Device 100 and its associated methods may enable the blink reflex device to measure the blink reflex for either eye (unilateral) or both eyes (bilateral) of the subject based on an intentional blink by the subject (e.g., a conscious blink in response to a command), a spontaneous blink of the subject (e.g., an unconscious blink to moisten or lubricate the eye), or a reflexive blink of the subject in response to one or more different types of stimulation (e.g., electrical, mechanical, acoustic, optical, or some other type of stimulation) directly to the eye, eye lid, eye lashes, or proximity of the eye (e.g., within ¼, ½, 1, 2, etc. inches of the eye or eyelid). The different types of stimulation may trigger different neural pathways within, and/or neurological functions of, the brain to cause the blink reflex. Thus, measuring the blink reflex using different types of stimulation may enable a type of neurological impairment within the brain to be identified and/or a specific location or structure, within the brain, that has been injured or impaired, to be identified.

Device 100 and its associated methods may enable the blink reflex device to compare the measured blink reflex, blink period, or a brain reflex to a baseline blink reflex, blink period, or some other brain reflex to identify an amount difference between the measured blink reflex, blink period, or brain reflex and the baseline blink reflex, blink period, or some other brain reflex, respectively The baseline measurement may correspond to a blink reflex, blink period, or brain reflex that is measured from the subject at a time when the subject is known not to be suffering from a neurological condition. For example, the baseline blink reflex, blink period, or brain reflex may be measured prior to the occurrence of a traumatic event, such as a blow to the head of the subject (e.g., on the field of play, on the battlefield, in a car accident, a physical altercation, etc.). Device 100 and its associated methods may also, or alternatively, enable the blink reflex device to determine whether the subject suffers from a neurological condition and/or the severity thereof based an amount of change between the measured blink reflex, blink period or brain reflex, and the baseline blink reflex, blink period and/or some other brain reflex, respectively. Additionally, or alternatively, the blink reflex device may enable the type of neurological condition and/or specific locations in the brain that have be injured to be identified based on a respective amount of change of the blink reflex, blink period and/or brain reflex for each of the different types of stimulation. Device 100 and its associated methods may also, or alternatively, enable the type of neurological condition and/or specific locations or structures of the brain that have been injured to be identified based on differences in the blink reflex and/or blink period between the left and right eye. Over time, device 100 and its associated methods may enable the blink reflex device to track changes in the baseline blink reflex, blink period, and/or brain reflex as a subject ages or is repeatedly exposed to brain or neurological trauma.

Additionally, or alternatively, device 100 and its associated methods may enable the blink reflex device to identify the type of degenerative neurological disorder based on an amount of change in non-stimulated blink period (e.g., between measured and baseline blink period) based on an intentional blink and/or spontaneous blink. Additionally, or alternatively, device 100 and its associated methods may enable a blink reflex device to sense and/or monitor the eye of the subject to measure the blink reflex, blink period, eye movement (e.g., the rate and/or amount of angular rotation of the eye), pupillary response (e.g., the rate and/or amount in which the pupil of the eye changes size), and/or brain activity (e.g., electrical signals of the brain, brain waves, etc.). The blink reflex device may detect potential impaired neurological function and/or the severity thereof based on a combination of changes in blink reflex and/or blink period and one or more other responses, such as changes in the subject's pupillary response, eye movement response, and/or changes in level of brain activity.

Device 100 and its associated methods may enable the blink reflex device to detect the potential for a neurological condition in a subject based on measuring the ability of the subject to normally respond to blink-inducing stimuli and/or spontaneous blink rates. Device 100 and its associated may enable the blink reflex device to aid a medical practitioner and/or user to determine the integrity of the afferent sensory system entering the brainstem of the subject, the efferent motor function of the subject, as well as general homeostasis maintenance activity, such as blink in lubrication of the eye. Thus, the change in blink reflex as measured by the blink reflex device, may provide the user in the field a decision aid regarding whether to permit a player to return to the playing field and/or the medical practitioner insight into whether and to what extent the deep brain structures have been altered or injured due to a traumatic event to the subject.

Device 100 and its associated methods, described herein, may enable a determination of whether a subject potentially suffers from a brain injury and/or a degenerative neurological condition. Device 100 and its associated methods may enable a blink reflex device to obtain information associated with a blink or other brain reflex, blink period, eye movement, or pupillary response of a subject. Device 100 and its associated methods may also, or alternatively, enable the blink reflex device to detect when the subject exhibits an abnormal blink (e.g., a micro-sleep, a double blink, etc.) and may reject, discard, and/or ignore any data, that corresponds to an abnormal blink. Device 100 and its associated methods may enable the blink reflex device to measure the blink reflex and/or blink period for either or both eyes of the subject based on an intentional blink by the subject, a natural blink of the subject, or a reflexive blink of the subject in response to one or more different types of stimuli (e.g., mechanical, light, acoustic, electrical, or some other type of stimuli).

Device 100 and its associated methods may enable the blink reflex device to compare information associated with a blink reflex and/or blink period obtained prior to a traumatic event experienced by the subject, with information associated with the blink reflex and/or blink period obtained after the traumatic event to identify an amount of change between the blink reflex and/or blink period before and after the trauma. Device 100 and its associated methods may also, or alternatively, enable the blink reflex device to determine whether the subject suffers from a neurological condition and/or the severity thereof based an amount of change in the blink reflex before and after the trauma relative to one or more thresholds. Additionally, or alternatively, the blink reflex device may lend insight into a type of brain injury and/or specific locations in the brain that have been injured as a result of the trauma based on a respective amount of change of the blink reflex and/or blink period for each of the different types of stimulation to the subject and/or based on differences in the blink reflex between the left and right eye.

Additionally, or alternatively, device 100 and its associated methods may enable the blink reflex device may lend insight into a type of degenerative neurological disorder based on an amount of change in non-stimulated blink reflex before and after trauma based on an intentional blink and/or spontaneous blink without stimulation. Additionally, or alternatively, device 100 and its associated methods may enable a blink reflex device to sense and/or monitor the eye of the subject to measure the blink reflex, blink period, eye movement (e.g., the rate and/or amount of angular rotation of the eye), pupillary response (e.g., the rate and/or amount in which the pupil of the eye changes size), and/or brain activity (e.g., electrical signals of the brain, brain waves, etc.). The blink reflex device may detect a neurological condition, and/or the severity thereof based on a combination of changes (e.g., before and after the subject experiences a traumatic event) in blink reflex and/or blink period relative to certain thresholds, and one or more known responses, such as changes in the subject's pupillary response, eye movement response, and/or brain activity, etc.

Device 100 and its associated methods may enable the blink reflex device to aid a user of the blink reflex device to determine the integrity of the afferent sensory system entering the brainstem of the subject as well as the efferent motor function of the subject. Thus, the change in blink reflex as measured by the blink reflex device, may provide the user in the field a decision aid regarding whether to permit a player to return to the playing field and/or the medical practitioner insight into whether and to what extent the deep brain structures have been altered or injured due to a traumatic event to the subject.

Device 100 and its associated methods may enable the blink reflex device to measure the blink reflex, blink period, and/or other brain reflex on an aggregate, population level to determine typical norms in development, growth, and/or aging processes and compare it to blink reflex and blink period numbers experienced by individual subjects. The metric obtained can be used to quantify deviations from population norms that will allow quantifiable measures of diagnoses that are currently described qualitatively.

FIG. 2 is a diagram of an example environment E in which the devices and methods, described herein, may be implemented. As shown in FIG. 2, environment E may include a group of user devices 110-1, . . . , 110-J (collectively referred to herein as "user devices 110," and individually as "user device 110") (where J≥1) a group servers 120-1, . . . , 120-K (collectively referred to herein as "servers 120" and individually as "server 120") (where K≥1), a blink reflex device 100 and a database 130, some or all of which are interconnected by a network 140. The number of devices and/or networks, illustrated in FIG. 2, is provided for explanatory purposes only. In practice, there may be additional networks and/or devices, fewer networks and/or devices, different networks and/or devices, or differently arranged networks and/or devices than illustrated in FIG. 2.

Also, in some implementations, one or more of the devices of environment E may perform one or more functions described as being performed by another one or more of the devices of environment E. Components of environment E may interconnect via wired connections, wireless connections, or a combination of wired and wireless connections.

User device 110 may include any computation or communication device, such as a wireless mobile communication device, that is capable of communicating with network 140. For example, user device 110 may include a radiotelephone, a personal communications system (PCS) terminal (e.g., such as a smart phone that may combine a cellular radiotelephone with data processing and data communications capabilities), a personal digital assistant (PDA) (e.g., that can include a radiotelephone, a pager, Internet/intranet access, etc.), a laptop computer, a tablet computer, a personal computer, a camera, a personal gaming system, or another type of computation or communication device.

User device 110 may further perform communication operations by sending data to or receiving data from another device, such as some other user device 110, server 120, blink reflex device 100, and/or database 130. User device 110 for example, receive an indication from blink reflex device 100 and/or server 120 that indicates whether and/or to what level of severity the subject suffers from a neurological condition. Data may refer to any type of machine-readable information having substantially any format that may be adapted for use in one or more networks and/or with one or more devices. Data may include digital information or analog information. Data may further be packetized and/or non-packetized. User device 110 may include logic for performing computations on user device 110 and may include the components illustrated in FIG. 2 in an example implementation.

Server 120 may include one or more server devices, or other types of computation or communication devices, that gather, process, search, store, and/or provide information in a manner described herein. Server 120 may communicate via network 140. Server 120 may receive from network 140 and/or blink reflex device 100 blink reflex information associated with a blink reflex of a subject (e.g., before and/or after a traumatic event to the head or spine of the subject) and may store such blink reflex information in a memory associated with server 120 and/or database 130. Server 120 may also, or alternatively, compare measured blink reflex information associated with a subject with baseline blink reflex information associated with the subject (e.g., obtained from database 130) and/or other subjects (e.g., obtained prior to a traumatic event experienced by the subject and/or other subjects and/or at a time that it was known that the subject and/or other subjects did not suffer from neurological condition to identify an amount of change between the measured blink reflex and the baseline blink reflex. Server 120 may, based on the amount of change between the measured blink reflex and the baseline blink reflex, determine whether and/or to what level of severity the subject may suffer from a brain injury and/or a degenerative neurological condition. Server 120 may provide an indication to blink reflex device 100, user device 110, or another server 120 indicating whether and/or to what level of severity the subject potentially suffers from a brain injury and/or a degenerative neurological condition.

Blink reflex device 100 may include one or more components that are capable of obtaining, measuring, or generating certain biometric information relating to a subject and communicating with network 140. For example, blink reflex device 100 may include a radiotelephone, a personal communications system (PCS) terminal (e.g., such as a smart phone that may combine a cellular radiotelephone with data processing and data communications capabilities), a personal digital assistant (PDA) (e.g., that can include a radiotelephone, a pager, Internet/intranet access, etc.), a laptop computer, a tablet computer, a personal computer, a camera, a personal gaming system, or another type of computation or communication device. Additionally, or alternatively, blink reflex device 100 may include one or more sensor components to detect all or a portion of the subject's body (e.g., all or portions of the subject's eyes, face, head, etc.) for the purposes of measuring a blink reflex, blink period, pupillary response, eye movement, subject identity, etc. associated with the subject. Blink reflex device 100 may also, or alternatively, include one or more components, to be described in greater detail in FIGS. 2 and 4, that may mechanically, electrically, optically, or acoustically stimulate the subject to cause the blink reflex in the subject.

Blink reflex device 100 may obtain blink reflex information from the subject (e.g., after a traumatic event to the head and/or spine of the subject) and may compare such information to other blink reflex information (e.g., baseline blink reflex information) associated with a blink reflex of the patent and/or other subjects (e.g., prior to any trauma and/or at a time when it was known that the subject did not suffer from impaired neurological function) to determine whether the subject suffers from a neurological condition. Blink reflex device 100 may communicate with server 120, database 130 and/or user device 110, via network 140, to transmit or receive information associated with a blink reflex of the subject and/or baseline blink reflex information associated with one or more other subjects. Additionally, or alternatively, blink reflex device 100 may include logic, such as one or more processing or storage devices, that can be used to perform and/or support processing activities in connection with the operation described herein.

Database 130 may include one or more devices that store information received from blink reflex device 100, and/or server 120. For example, database 130 may store information associated with a blink reflex, blink period, eye movement, pupil response, etc. relating to one or more subject. Database 130 may also, or alternatively, store in formation associated with the subject (e.g., name, age, gender, race, etc.), information associated with test conditions or parameters (e.g., with or without confounding, a type of stimulation, a type of measurement, etc.), and/or information describing a type of trauma or condition (e.g., football injury, automobile accident, pre-existing condition suffered by subject, etc.).

Network 140 may include one or more wired and/or wireless networks. For example, network 140 may include a cellular network, a public land mobile network (PLMN), a second generation (2G) network, a third generation (3G) network, a fourth generation (4G) network (e.g., a long term evolution (LTE) network), a fifth generation (5G) network, and/or another network. Additionally, or alternatively, network 140 may include a wide area network (WAN), a metropolitan network (MAN), a telephone network (e.g., the Public Switched Telephone Network (PSTN)), an ad hoc network, an intranet, the Internet, a fiber optic-based network, and/or a combination of these or other types of networks.

FIG. 2 is a diagram of example components of blink reflex device 100. As shown in FIG. 2, blink reflex device 100 may include a processing unit 200, a stimulator 102, a memory 210, a sensor unit 215, a user interface 220, a communication interface 230, and/or an antenna assembly 240. Although FIG. 2 shows example components of blink reflex device 100, additionally, or alternatively, blink reflex device 100 may include fewer components, additional components, different components, or differently arranged components than depicted in FIG. 2. In still other implementations, one or more components of blink reflex device 100 may perform one or more tasks described as being performed by one or more other components of blink reflex device 100.

Processing unit 200 may include a processor, a microprocessor, an application specific integrated circuit (ASIC), a field programmable gate array (FPGA), or the like. Processing unit 200 may control operation of blink reflex device 100 and its components. In one implementation, processing unit 200 may control operation of components of blink reflex device 100 in a manner similar to that described herein. For example, processing unit 200 may instruct stimulator 102 to apply a mechanical, optical, acoustic or electrical stimulation to the subject. Additionally, processing unit 200 may repeat the instruction based on a time interval, randomly (e.g., based on a random number generated by processing unit 200), and/or in response to an instruction from a user of blink reflex device 100.

Memory 210 may include a RAM, a ROM, and/or another type of memory to store data and/or instructions that may be used by processing unit 200. Memory 210 may store information associated with a blink reflex of a subject that is received from sensor unit 215, another component of blink reflex device 100 and/or network 140.

Sensor unit 215 may include one or more components to detect, measure, scan, and/or record all or a portion of a body of a subject, such as, for example, the face, the eyes, a portion of one or both of the eyes (e.g., eyelid, a pupil, etc.), etc. For example, sensor unit 215 may include one or more a cameras, photodiodes, electro-optical sensors, infrared sensors, ultraviolet sensors, laser diode sensors, electrodes, focal plan arrays (FPA), antenna, etc. to detect, measure, scan, and/or record the subject (e.g., the eye, eyelid, face, etc. of the subject) in one or more portions of the electromagnetic spectrum (e.g., ultraviolet, visual, thermal, far infrared, microwave, electrical, x-ray, etc.). Sensor unit 215 may include a field of view, directivity, scan rate (e.g., scans per minute, per second, etc.), pixel density (e.g., pixels per line or array), spectral range, dynamic range, level of resolution (e.g., dots per inch), a frame rate, a shutter speed, gain control, etc. that enables the eye, eyelid, eyelashes, etc. of the subject to be detected and tracked as a function of time before, during, and after stimulation is applied and/or the subject intentionally or unintentionally blinks. In one example, sensor unit 215 may measure information associated with a blink reflex of the subject and may provide such information to processing unit 200. Additionally, or alternatively, sensor unit 215 may measure other information associated with eye movement, pupillary response, brain waves, etc. associated with the subject and may provide such other information to processing unit 200.

User interface 220 may include one or more components that enable information to be input blink reflex device 100 and/or for outputting information from blink reflex device 100. For example, user interface may include buttons, a touch screen, control buttons, a keyboard, a pointing device, etc. to enable a user, of blink reflex device 100, to input information associated with a measurement (e.g., type and/or magnitude of stimuli; selection of right, left or both eyes, retrieval of information associated with baseline blink reflex, to power up, to power down, etc.) and/or to permit data and control commands (e.g., on, off, record, play, etc.) to be input into blink reflex device 100 via user interface 220. User interface 220 may also, or alternatively, render video, images, audio, graphical, or textual information associated with a blink reflex of the subject for display to enable the subject or medical practitioner to determine whether the subject potentially suffers from a neurological condition or the severity thereof.

Communication interface 230 may, for example, include one or more components that enable blink reflex device 100 to communicate with network 140 via transmit/receive 240. For example, communication interface 230 may include a transmitter that converts baseband signals from processing unit 200 to signals (e.g., microwave signals, infrared signals, etc.) that can be transmitted, via transmit/receive 240 to network 140. Communication interface 230 may also, or alternatively, include a receiver that converts signals received from transmit/receive 240 to baseband electrical or optical signals that can be processed by processing unit 200. Additionally, or alternatively, communication interface 230 may include a transceiver to perform functions of both a transmitter and a receiver of wireless communications (e.g., radio frequency, infrared, visual optics, etc.), wired communications (e.g., conductive wire, twisted pair cable, coaxial cable, transmission line, fiber optic cable, waveguide, etc.), or a combination of wireless and wired communications.

Transmit/receive 240 may include one or more antennas to transmit and/or receive radio frequency (RF) signals over the air. Transmit/receive 240 may, for example, receive RF signals from communication interface 230 and transmit them over the air, and receive RF signals over the air and provide them to communication interface 230. Additionally, or alternatively, transmit/receive 240 may include one or more optical devices to transmit and/or receive optical signals (e.g., visual, infrared, laser, ultraviolet, etc.) over the air. Transmit/receive 240 may, for example, receive optical signals from communication interface 230 and transmit them over the air, and/or receive optical signals over the air and provide them to communication interface 230.

As described in detail below, blink reflex device 100 may perform certain operations described herein in response to processing unit 200 executing software instructions of an application contained in a computer-readable medium, such as memory 210. The software instructions may be read into memory 210 from another computer-readable medium or from another device via communication interface 230. The software instructions contained in memory 210 may cause processing unit 200 to perform processes that will be described later. Alternatively, hardwired circuitry may be used in place of or in combination with software instructions to implement processes described herein. Thus, implementations described herein are not limited to any specific combination of hardware circuitry and software.

Figure 4:
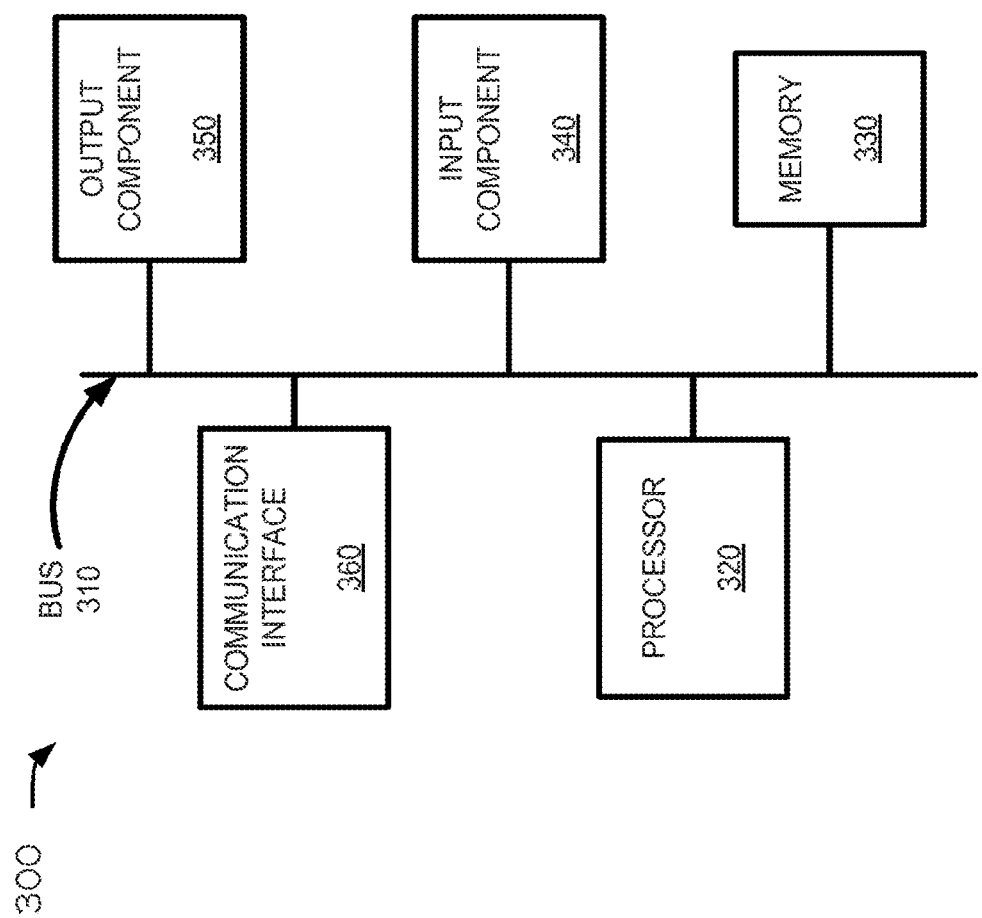
FIG. 4 is a diagram of example components that may correspond to one or more of the devices and/or components of FIGS. 1A-3.

FIG. 4 is a diagram of example components of a device 300 that may correspond to user device 110, server 120, and/or blink reflex device 100 (e.g., processing unit 200). Alternatively, each of user device 110, server 120, and/or blink reflex device 100 may include one or more devices 300. Although FIG. 4 shows example components of device 300, additionally, or alternatively, device 300 may include fewer components, additional components, different components, or differently arranged components than depicted in FIG. 4. Additionally, or alternatively, one or more components of device 300 may perform one or more tasks described as being performed by one or more other components of device 300.

Device 300 may include a bus 310, a processor 320, a memory 330, an input component 340, an output component 350, and a communication interface 360. Although FIG. 4 shows example components of device 300, in other implementations, device 300 may contain fewer components, additional components, different components, or differently arranged components than depicted in FIG. 4. For example, device 300 may include one or more switch fabrics instead of, or in addition to, bus 310. Additionally, or alternatively, one or more components of device 300 may perform one or more tasks described as being performed by one or more other components of device 300.

Bus 310 may include a path that permits communication among the components of device 300. Processor 320 may include a processor, microprocessor, or processing logic that may interpret and execute instructions. Memory 330 may include any type of dynamic storage device that may store information and instructions, for execution by processor 320, and/or any type of non-volatile storage device that may store information for use by processor 320.

Input component 340 may include a mechanism that permits a user to input information to device 300, such as a keyboard, a keypad, a button, a switch, etc. Output component 350 may include a mechanism that outputs information to the user, such as a display, a speaker, one or more light emitting diodes (LEDs), etc. Communication interface 360 may include any transceiver-like mechanism that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. For example, communication interface 360 may include mechanisms for communicating with another device or system via a network, such as network 140. In one alternative implementation, communication interface 360 may be a logical component that includes input and output ports, input and output systems, and/or other input and output components that facilitate the transmission of data to other devices.

As will be described in detail below, device 300 may perform certain operations relating to video content ingestion. Device 300 may perform these operations in response to processor 320 executing software instructions contained in a computer-readable medium, such as memory 330. A computer-readable medium may be defined as a non-transitory memory device. A memory device may include space within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of or in combination with software instructions to implement processes described herein. Thus, implementations described herein are not limited to any specific combination of hardware circuitry and software.

Mechanical module 410 may, for example, include a component that outputs a mechanical stimulation, such as, for example, a puff of fluid at a predetermined pressure, direction, quantity, velocity, duration, etc. The term fluid, as used herein, includes a gas, liquid, or any material the flows or behaves in a like manner (e.g., nitrogen, air, water, water vapor, etc.). The puff of fluid may be directed to one or both eyes of the subject or within proximity of the eye and/or eyelid (e.g., within one-quarter inch, on-half inch, one inch, one and one-half inch, etc. of the eye, eyelid, eyelashes, etc.) to cause the subject to exhibit a blink reflex. Mechanical module 410 may also, or alternatively, include a component that applies a controlled mechanical pressure to the proximity of the eye and/or eyelid (e.g., a pin prick, a pinch, etc.).

Light module 420 may include a component (e.g., a light bulb, flash tube, a light emitting diode (LED), etc.) that outputs light (e.g., a flash of light, continuous light, a blinking light, etc.) at a controlled and/or predetermined intensity level, power level, frequency, duration, etc. directed to one or both eyes of the subject to cause the subject to exhibit a blink reflex.

Acoustic module 430 may include a component (e.g., a speaker, head phones, ear buds, etc.) that outputs an acoustic signal (e.g., a tone, white noise, rock music, etc.) at a controlled and/or predetermined volume, frequency, duration, etc. that causes the subject to exhibit a blink reflex.

Additionally, electrical module 440 may include a component (e.g., electrodes, contacts, etc.) that outputs an electrical signal at a predetermined power level (e.g., current, voltage, etc.), frequency, duration, etc. that may be perceived by the subject as a small shock and which may cause the subject to exhibit a blink reflex. Stimulator 102 may also, or alternatively, include a device capable of measuring the brain activity of the subject before, during, or after the subject is stimulated by stimulator 102.

Confounder Module 450 include a device to confound or distract the subject so as to attenuate a tendency by the subject to anticipate certain stimuli provided by stimulator 102, which may affect the integrity of the data. Confounder module 450 may include one or more lights can be turned on or off, one or more speakers that emit one or a series of tones, a user interface displayed via a display device via which questions, objects, games, etc. are provided. For example, the subject may interact with confounder module 450 by identifying which lights turn on or off; by indicating whether an acoustic tone can be heard, whether the tone pitch is increasing, decreasing, or staying the same; by answering questions and/or interacting with objects displayed via the user interface, etc.

Figure 6A:
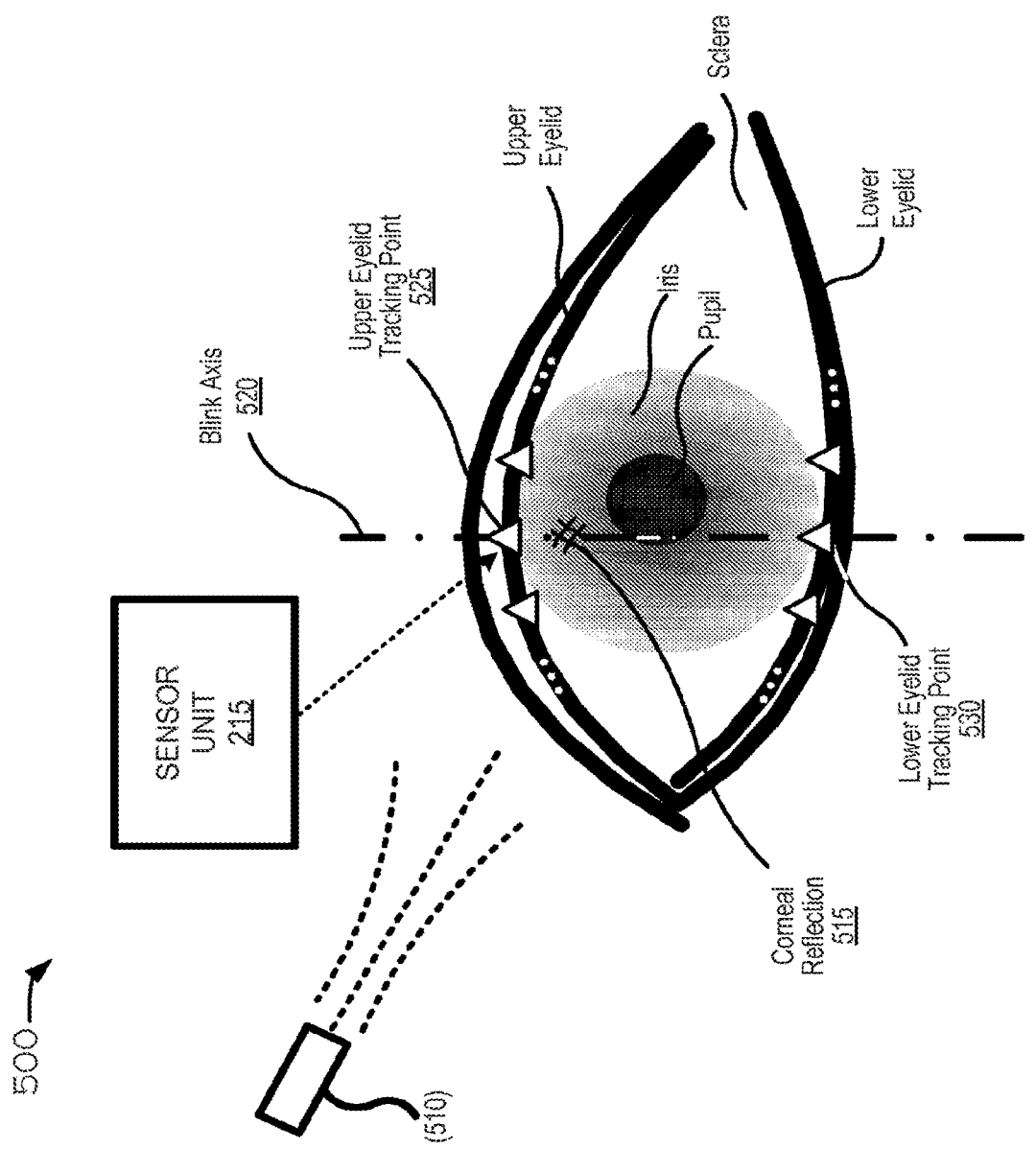
FIG. 6A is a diagram of an example eyelid tracking scheme associated with measuring a blink reflex of a subject.

FIG. 6A is a diagram of an example eyelid tracking scheme 500 (hereinafter, "tracking scheme 500") associated with a subject. In an example implementation, tracking scheme may be used by blink reflex device 100 to perform an operation to determine a blink reflex and/or a blink period of a subject by measuring, as a function of time, the location of all or a portion of one or both eyelids when the subject initiates a blink, performs the blink, and/or completes the blink. As shown in FIG. 6A, tracking scheme 500 may include light source 510, a corneal reflection 515, a blink axis 520, an upper eyelid tracking point 525, and a lower eyelid tracking point 530. Light source 510 may include a light bulb, an LED, a low power laser that does not cause damage to the eye (e.g., less than approximately 5 milliwatts (mW), etc.) that emits light that can be directed to an eye of the subject. Light source 510 may also, or alternatively, be associated with stimulator 102 and/or some other component of blink reflex device 100.

By way of example, light source 510 may emit a beam of light (e.g., as shown by the dotted line between light source 510 and the iris of the eye in FIG. 6A) in a manner that is incident on the cornea portion (e.g., a membrane that covers the iris and pupil portions of the eye) of the eye of a subject. The beam of light may enter the cornea and/or may reflect off the cornea and/or iris portion of the eye to cause a reflection of light to appear on a portion of the surface of the eye (e.g., shown by the "#" labeled corneal reflection 515). Sensor unit 215 may detect corneal reflection 515 and may identify a first point along an approximately vertical blink axis 520 (e.g., shown as the alternating dashed and dotted vertical line labeled "blink axis 520") at which the upper eyelid intersects blink axis 520 (e.g., shown as a "Δ" labeled "upper eyelid tracking point 525" in FIG. 6A). Additionally, or alternatively, sensor unit 215 may detect corneal reflection 515 and may identify a second point along blink axis 520 at which the lower eyelid intersects blink axis 520 (e.g., shown as an "A" labeled "lower eyelid tracking point 530" in FIG. 6A).

Additionally, or alternatively, sensor unit 215 may monitor and/or track the movement of the upper eyelid (e.g., before, during, and/or after the subject blinks) based on the upper eyelid tracking point 525 and/or the lower eyelid tracking point 530. Sensor unit 215 may also, or alternatively, identify one or more different upper eyelid tracking points 525 associated with the upper eyelid (e.g., shown by the other "As" located on the upper eyelid of FIG. 6A) and may monitor and/or track the vertical position of one, some, or all of the different upper eyelid tracking points 525 (e.g., based on each individual vertical position, a sum of the vertical positions, an average of the vertical positions, etc. of the different upper eyelid tracking points 525). Sensor unit 215 may also, or alternatively, monitor and/or track the vertical position of one, some, or all of the different lower eyelid tracking points 530 in a manner similar to that described above.

Additionally, or alternatively, sensor unit 215 may track upper eyelid tracking points 525 and/or lower eyelid tracking points 530 in a generally horizontal direction that is approximately orthogonal to blink axis 520. Additionally, or alternatively, sensor unit 215 may identify a tracking point that enables the movement of the eye to be tracked, for example, in the vertical direction, the horizontal direction, or some other direction. In this example, sensor unit 215 may track the change in location of corneal reflection 515 to determine eye movement. Additionally, or alternatively, sensor unit may identify some other tracking point, associated with the eye or portion thereof (e.g., an edge of the iris, the pupil, etc.).

Figure 6B:
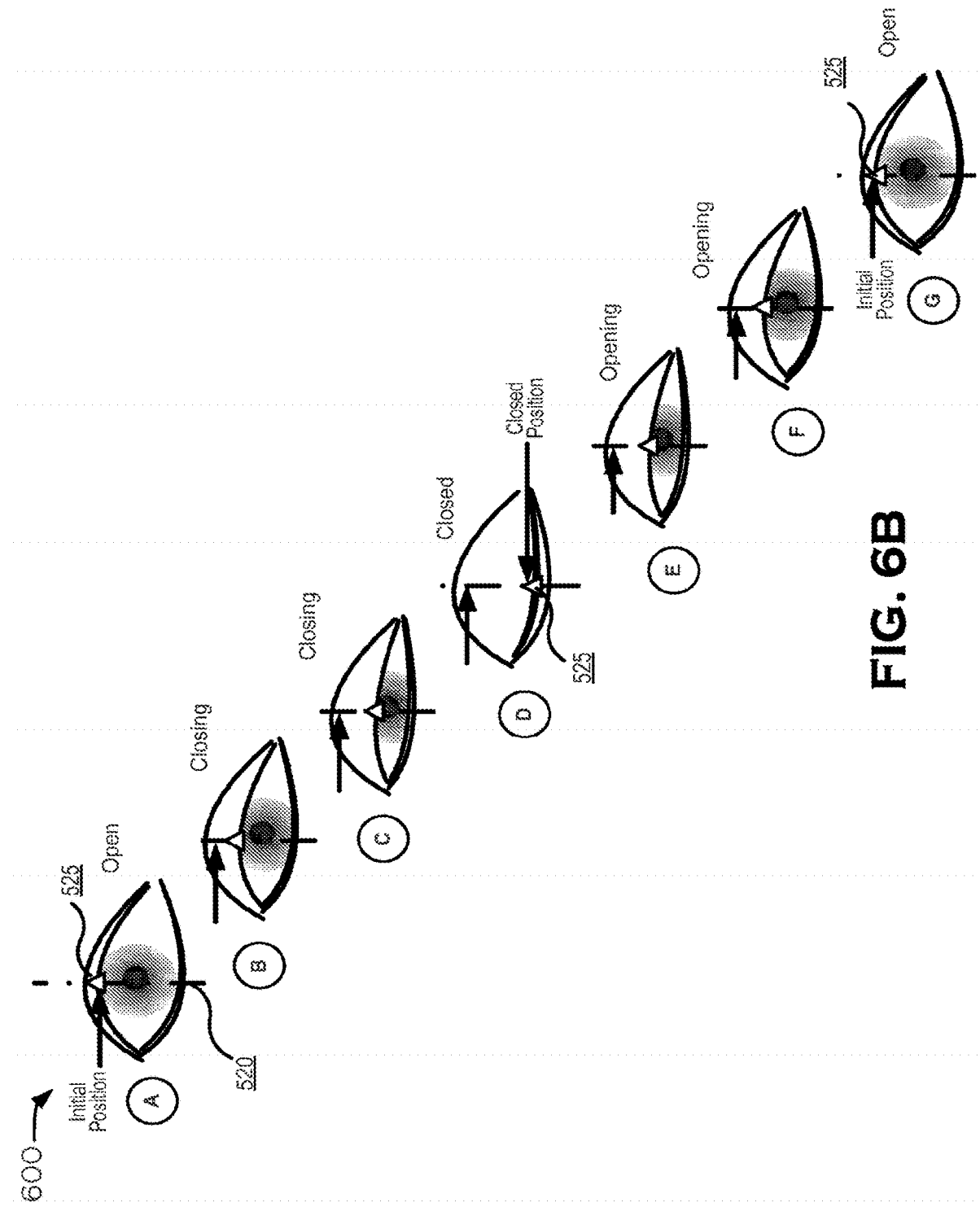
FIG. 6B is a diagram of example stages of a blink of an eye of a subject from which a blink reflex can be measured.

FIG. 6B is a diagram of example stages 600 of a blink of an eye of a subject from which a blink reflex or blink period can be measured. As shown in FIG. 6B, eye blink stages 600 may include a collection of eye blink stages A through G associated with the blink of the eye of the subject. The number of eye blink stages of FIG. 6B is provided for explanatory purposes. In practice, there may be additional stages, fewer stages, or different stages than are shown in FIG. 6B. While stages 600 is described in the context of upper eyelid tracking point 525, associated with the upper eyelid of the subject, additionally, or alternatively, stages 600 may be described in the context of one or more different upper eyelid tracking points 525 and/or one or more lower eyelid tracking points 530 associated with the lower eyelid of the subject.

Eye blink stage A may correspond to a first state of the eye of the subject at a first time prior to the initiation of a blink. During eye blink stage A, the eye may be open and/or the location of upper eyelid tracking point 525 may correspond to an initial position (e.g., shown as the righting pointing arrow labeled "Initial Position" in FIG. 6B) on the approximately vertical blink axis 520 with which upper eyelid tracking point 525 coincides. Eye blink stage B may correspond to a second state of the eye at a second time after the initiation of a blink when the upper eyelid and/or lower eyelid begins to close. During eye blink stage B, the eye may begin closing and/or the location of upper eyelid tracking point 525 may correspond to a first position on the vertical axis that is located below the initial position on the vertical axis. Eye blink stage C may correspond to a third state of the eye of the subject at a third time that occurs after the second time. During eye blink stage C, the eye may be continuing to close and/or the location of upper eyelid tracking point 525 may correspond to a second position on blink axis 520 that is located below the first position. Eye blink stage D may correspond to a fourth state of the eye of the subject at a fourth time that occurs after the third time. During eye blink stage D, the eye may be closed and/or the location of upper eyelid tracking point 525 may correspond to a third position (e.g., shown as the "closed position" in FIG. 6B) on blink axis 520 that is located below the second position. In implementations in which lower eyelid tracking point 530 (not shown in FIG. 6B) is being monitored and/or tracked by blink reflex device 100, upper eyelid tracking point 525 and lower eyelid tracking point may be located at approximately the same position on blink axis 520.

Eye blink stage E may correspond to a fifth state of the eye of the subject at a fifth time that occurs after the fourth time. During eye blink stage E, the eye may begin opening and/or the location of upper eyelid tracking point 525 may correspond to a fourth position on blink axis 520 that is located above the third position. Eye blink stage F may correspond to a sixth state of the eye of the subject at a sixth time that occurs after the fifth time. During eye blink stage F, the eye may continue opening and/or the location of upper eyelid tracking point 525 may correspond to a fifth position on blink axis 520 that is located above the fourth position. Eye blink stage G may correspond to a sixth state of the eye of the subject at a sixth time that occurs after the fifth time. During eye blink stage G, the eye may be open and/or the location of upper eyelid tracking point 525 may correspond to a sixth position on blink axis 520 that is located above the fifth position. Additionally, or alternatively, the sixth position may coincide approximately with the location of the initial position of eye blink stage A. If this location is deemed significantly different than the initial position of the eye, it may also be an additional indicator that there is altered brain function suggestive of brain injury by comparison with known prior baselines in the database for the subject.

Figure 6C:
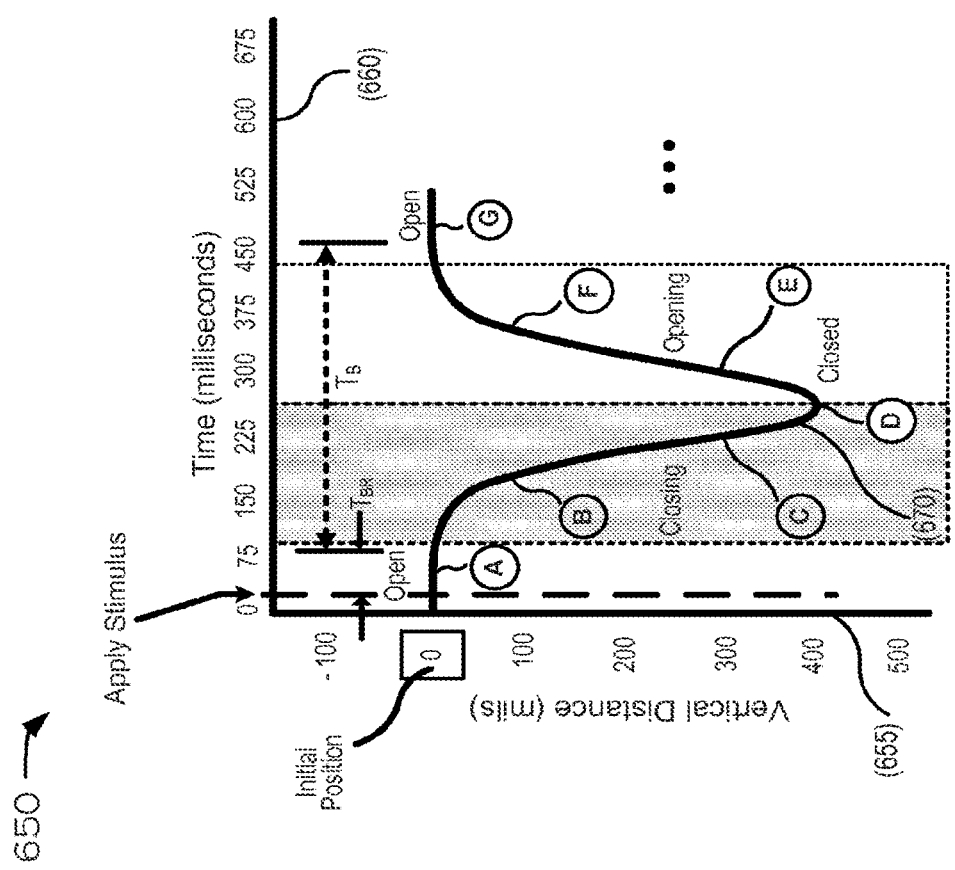
FIG. 6C is a diagram of an example blink reflex response associated with a subject.

FIG. 6C is a diagram of an example blink reflex response 650 (hereinafter, "response 650") associated with a blink reflex and blink period of a subject. Response 650 may be measured and/or created by blink device 100 based on a blink reflex and/or blink period associated with an eye of a subject. As shown in FIG. 6C, response 650 may include a distance scale 655, a time scale 660, and a blink function 670 (hereinafter, "blink function 670"). Distance scale 655 may include a range of distance (e.g., shown as the vertical axis labeled "Vertical Distance (mils)" ranging from −100 mils to +500 mils) that the upper eyelid tracking point 525, lower eyelid tracking point 530, or a combination of upper and lower eyelid tracking points 525 and 530, respectively, travel relative to an initial position on blink axis 520 when the subject blinks. Time scale 655 may include a range of time (e.g., shown as the horizontal axis labeled "Time (milliseconds)" ranging from 0 to 675 ms or some other period of time) during which the eye of the subject blinks one or more times. Blink function 670 may represent a relationship between a vertical distance that the eyelid travels (e.g., upper eyelid tracking point 525, lower eyelid tracking point 530 or some combination thereof) as shown on distance scale 655 as a function of time on time scale 660 when the subject blinks. The vertical dashed line labeled "Apply Stimulus" may identify a time (e.g., based on time scale 655) at which stimulation is applied to the subject.

Blink reflex device 100 may measure the blink reflex of a subject and may create blink function 670 based on the distance traveled by one or both eyelids of the subject as a function of time. For example, blink reflex device 100 may, in a manner similar to that described with respect to FIG. 6C, begin to track an eyelid tracking point (e.g., upper eyelid tracking point 525, lower eyelid tracking point 530 and/or some combination thereof) of the subject (e.g., at T=0 on time scale 660) and may apply a stimulus to the subject (e.g., with a puff of fluid, a mechanical, acoustic, electrical optical etc. stimulus). Blink reflex device 100 may track the movement of the eyelid tracking point and may identify a time at which eyelid tracking point begins to move vertically relative to blink axis 520 and/or a blink is initiated by the subject in response to the stimulus. Blink reflex device 100 may determine a time period from the time when the stimulus is applied to when the eyelid tracking point begins to move or the blink is initiated (onset). The time period may correspond to the blink reflex (e.g., shown as $T_{BR}$ in FIG. 6C).

Additionally, or alternatively, blink reflex device 100 may measure the blink period associated with the phases of the blink, the aggregate curve referred to as the morphology of the blink. For example, when the eye of the subject is in the open state (e.g., stage A of FIG. 6B), blink reflex device 100 may determine that the eyelid (e.g., upper eyelid tracking point 525, lower eyelid tracking point 530, or some combination thereof) is located at the initial position on distance scale 655 (e.g., approximately 0 mils) as shown by blink function 670 (e.g., shown as prior to 75 ms on time scale 660). When the eye of the subject is closing (e.g., stages B and C of FIG. 6B), blink reflex device 100 may determine that the tracking point of the eyelid has changed to a different position relative to the initial position (e.g., 50, 100, 150, 250, 350, etc. mils on distance scale 655) as shown by blink function 670 (e.g., shown as between approximately 75 and 250 ms on time scale 660). When the eye of the subject is in the closed state (e.g., stage D of FIG. 6B), blink reflex device 100 may determine that the eyelid tracking point is located a greatest distance from the initial position on distance scale 655 (e.g., shown as approximately 400 mils) as shown by blink function 670 (e.g., shown as between approximately 251 and 275 ms on time scale 660).

Additionally, or alternatively, when the eye of the subject is opening (e.g., stages E and F of FIG. 6B), blink reflex device 100 may determine that the tracking point of the eyelid has changed to a different position relative to the initial position (e.g., 50, 100, 150, 250, 350, etc. mils on distance scale 655) as shown by blink function 670 (e.g., shown as between approximately 275 and 450 ms on time scale 660). When the eye of the subject has returned to the open state (e.g., stage G of FIG. 6B), blink reflex device 100 may determine that the eyelid (e.g., upper eyelid tracking point 525, lower eyelid tracking point 530, or some combination thereof) has returned to the approximate initial position on distance scale 655 (e.g., approximately 0 mils) as shown by blink function 670 (e.g., shown as after 450 ms on time scale 660).

Blink reflex device 100 may determine a time period (the blink period or sometimes referred to as "blink duration") for the eye lid to travel from the initial position, to the closed position and return to the initial position (e.g., shown as $T_B$ in FIG. 6C).

FIGS. 7A-7D are diagrams of example blink reflex devices 100 through 100 that correspond to blink reflex device 100 associated with different stimulator modules 410-440, respectively. As shown in FIGS. 7A-7D, each of blink reflex devices 100-100 may include a housing 101 and one or more components described above with respect to FIG. 3 including processing unit 200, stimulator 102, and sensor 215. Housing 101 may include a material of sufficient strength, structure, and/or rigidity to enable some or all of the components, described above with respect to FIG. 3, to be attached and to operate in order to measure a blink reflex associated with a subject. Housing 101 may also, or alternatively, have a shape that corresponds to a subject's face so as to securely cover one or both eyes of the subject (e.g., similar to a scuba mask, goggles, etc.), worn by the subject, or in which all or a portion of the head of the subject can be inserted in a manner that enables stimulator 102 and/or sensor 215 sufficient line of sight to the eye or proximity thereof. While other components described with respect to FIG. 3, including memory 210, user interface 220, communication interface 230 and transmit/receive 240, are not shown in FIGS. 7A-7D for simplicity, in practice, blink reflex devices 100-100 may include one or more such components of FIG. 3, and/or additional components, fewer components, different components or differently arranged components than are described with respect to FIGS. 7A-7D.

Figure 7A:
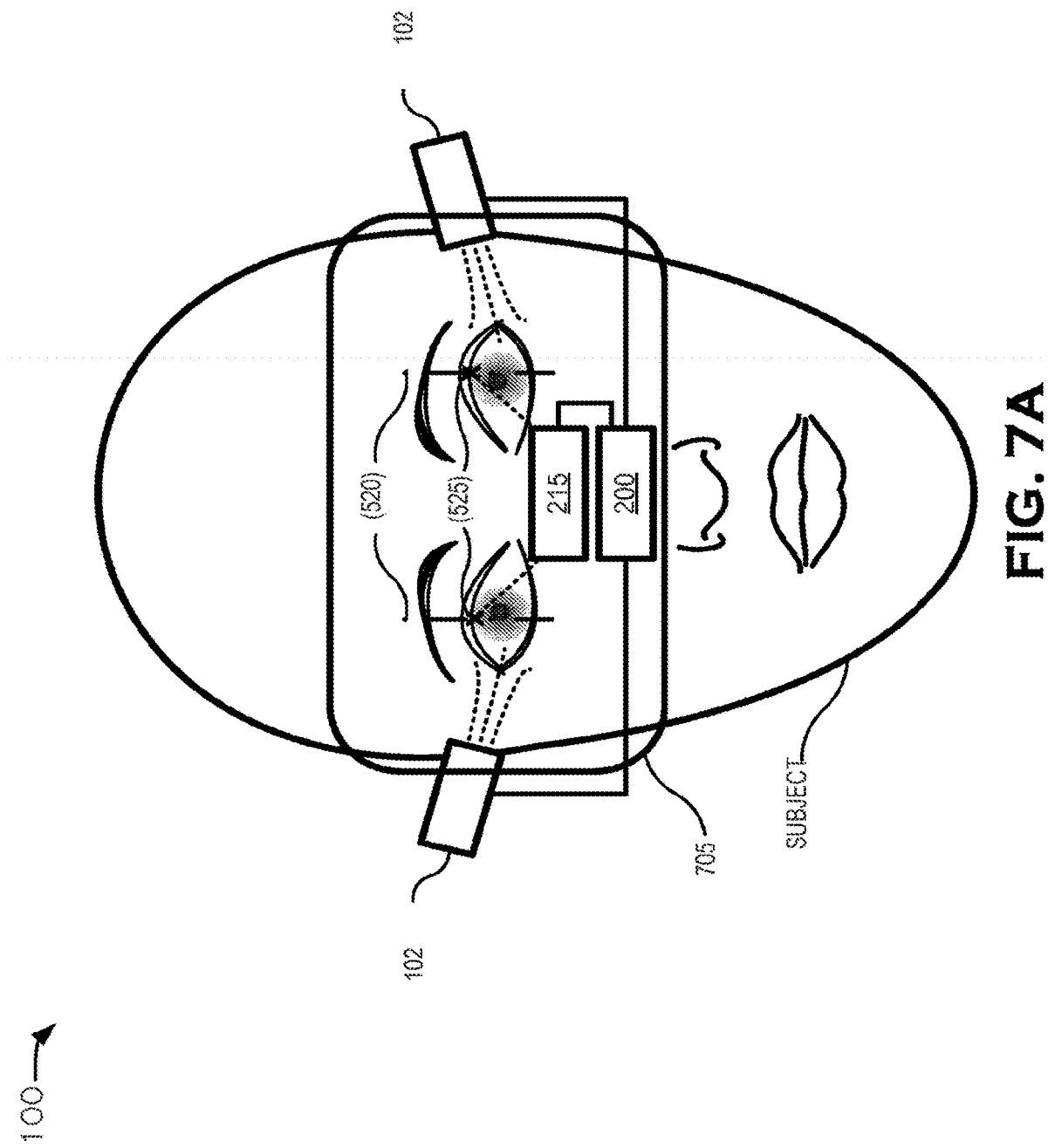

As shown in FIG. 7A, blink reflex device 100 may include housing 101, stimulator 102, sensor 215, processing unit 200 and one or more other components described above with respect to FIG. 3 (not shown in FIG. 7A). Stimulator 102 may include one or more mechanical modules 410. As shown in FIG. 7A, stimulator 102 may include a pair of mechanical modules 410-1 and 410-2. Mechanical module 410-1 may be associated with the right eye of the subject and mechanical module 410-2 may be associated with the left eye of the subject. One or both mechanical modules 410 may output a puff of fluid (e.g., air, nitrogen, water, water vapor, etc.) in the direction of one or both eyes of the subject. The puff of fluid may make contact with one or both eyes of the subject under sufficient velocity and/or pressure in a manner that causes a blink reflex in the subject that can be detected and measured by sensor 215 in a manner similar to that described above with respect to FIGS. 5, 6A and 6B (e.g., by tracking the movement of upper eyelid tracking point 525 and/or lower eyelid tracking point 530 (not shown in FIG. 7A)). Mechanical module 410 may also, or alternatively, be installed in and/or attached to housing 101. Additionally, or alternatively, mechanical module 410 may output the puff of air based on an instruction received from processing unit 200 and/or may output a signal to processing unit 200 indicating that the puff of air has been output by mechanical module 410.

Figure 7B:
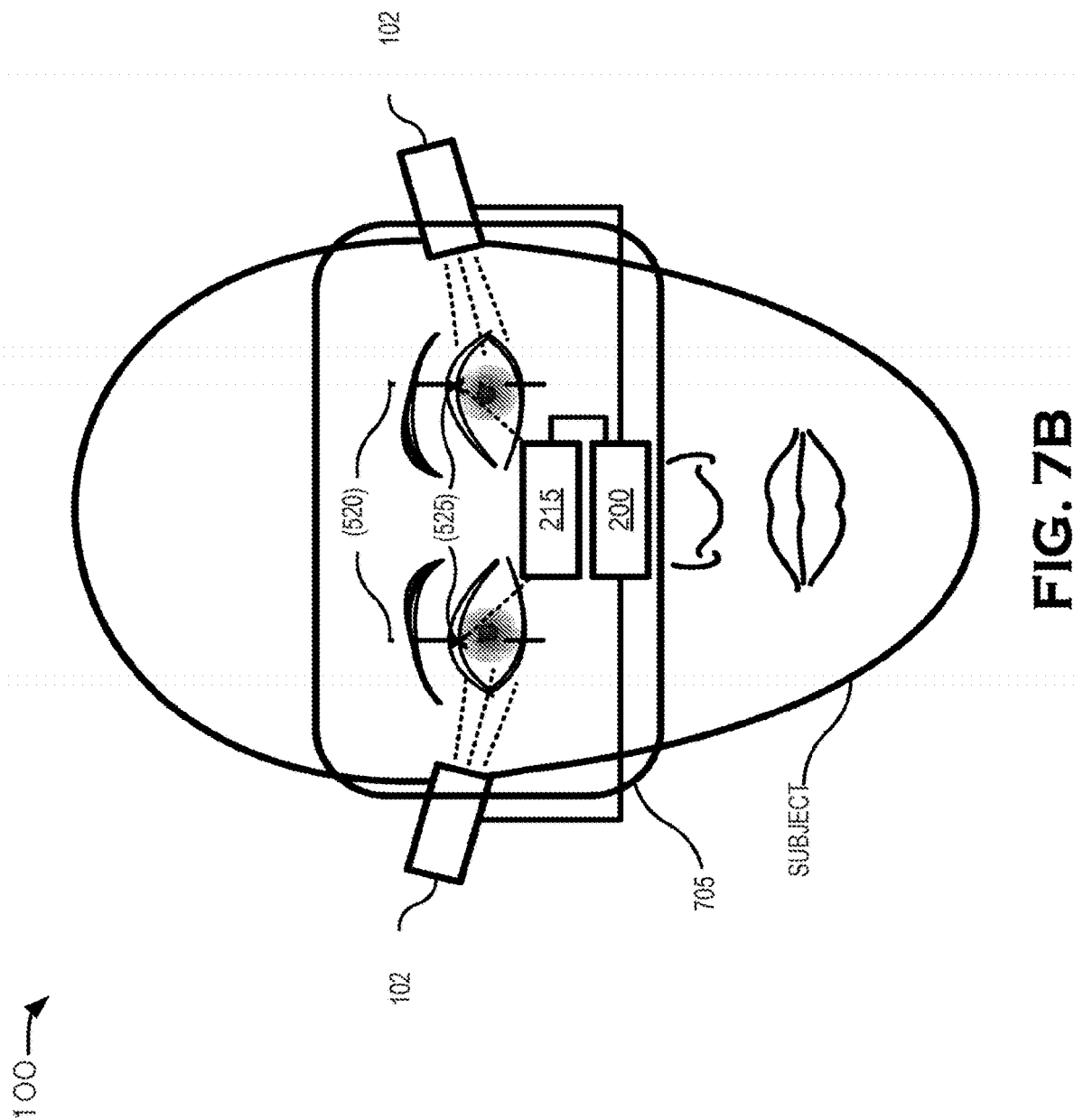

As shown in FIG. 7B, blink reflex device 100 may include some or all of the components described with respect to FIG. 7A. Stimulator 102 may include one or more optical modules 420 (e.g., optical modules 420-1 for the right eye and 420-2 for the left eye). One or both optical modules 420 may output one or more beams of light that shines in the direction of one or both eyes of the subject. The light may be of sufficient brightness and intensity to causes a blink reflex to occur in the subject, which can be detected and measured by sensor 215 in a manner similar to that described above with respect to FIGS. 5, 6A and 6B. Optical module 410 may also, or alternatively, be installed in and/or attached to housing 101. Additionally, or alternatively, optical module 420 may output the beam of bright light based on an instruction received from processing unit 200 and/or may output a signal to processing unit 200 indicating that the beam of bright light has been output by optical module 420.

Figure 7C:
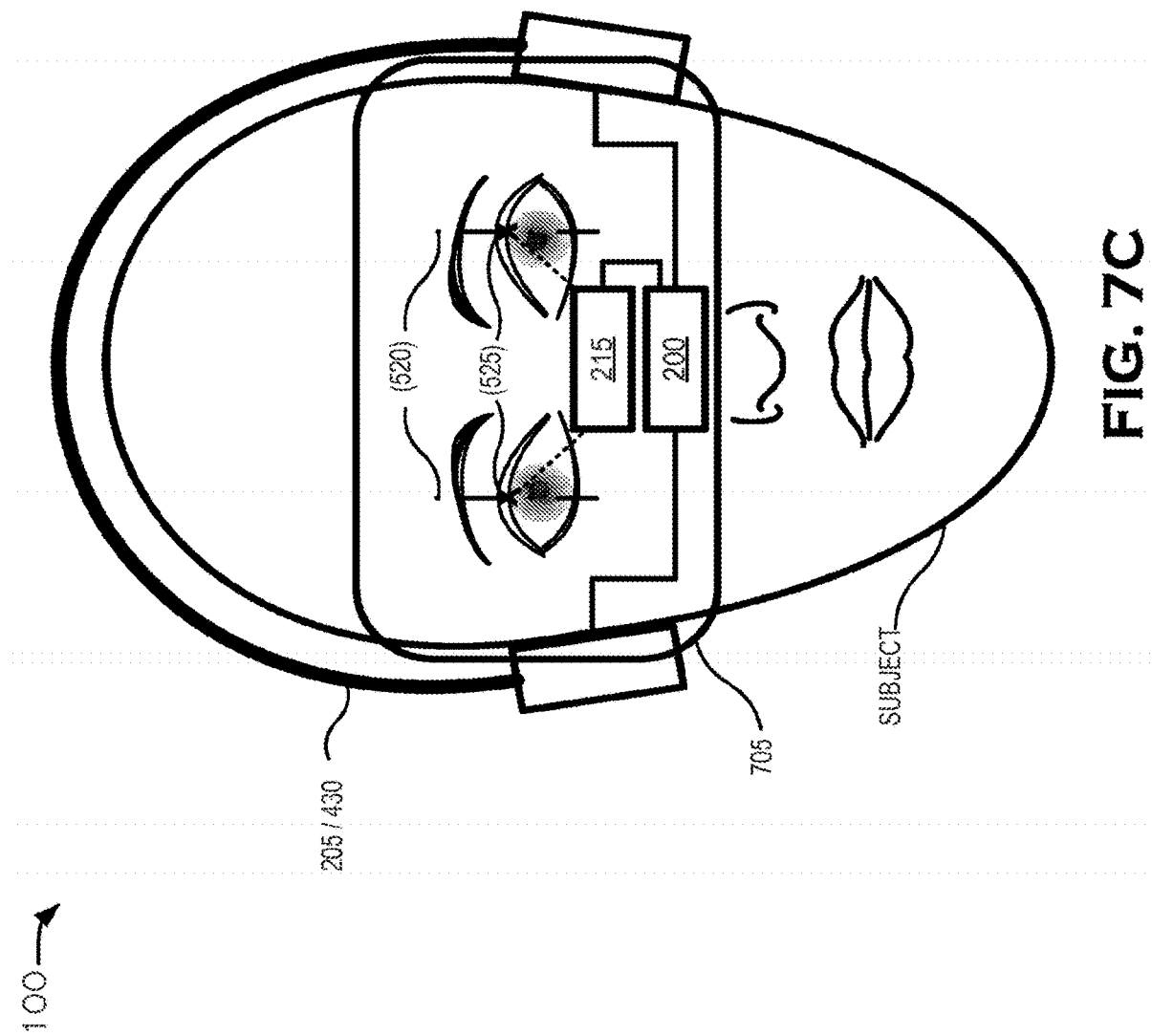

As shown in FIG. 7C, blink reflex device 100 may include some or all of the components described with respect to FIGS. 7A and/or 7B. Stimulator 102 may include one or more acoustic modules 430, such as, for example, a set of head phones, one or more ear buds, one or more speakers, etc. As shown in FIG. 7C, acoustic module 430 includes a set of headphones that are worn by the subject. Acoustic module 430 may output one or more acoustic tones, noise (e.g., white noise, pink noise, etc.), music (e.g., rock music, heavy metal, etc.), etc. (hereinafter, the "acoustic signal") into one or both ears of the subject. The acoustic signal may be of sufficient volume and frequency to be heard by the subject and to causes a blink reflex to occur in the subject, which can be detected and measured by sensor 215 in a manner similar to that described above with respect to FIGS. 5, 6A and 6B. Acoustic module 430 may also, or alternatively, be installed in and/or attached to housing 101. Additionally, or alternatively, acoustic module 430 may output the acoustic signal based on an instruction received from processing unit 200 and/or may output a signal to processing unit 200 indicating that the acoustic signal has been output by acoustic module 430.

As shown in FIG. 7D, blink reflex device 100 may include some or all of the components described with respect to FIGS. 7A-7C. Stimulator 102 may include one or more electrical modules 440 (e.g., electrical modules 440-1 for the right eye and 440-2 for the left eye). One or both optical modules 440 may output one or more electrical signals in the proximity of one or both eyes of the subject (e.g., within ¼ inch, ½ inch, 1 inch, 1½ inches, 2 inches, etc.). The electrical signal may be of sufficient power, signal strength, voltage, current, etc. to cause a blink reflex to occur in the subject, which can be detected and measured by sensor 215 in a manner similar to that described above with respect to FIGS. 5, 6A and 6B. Electrical module 440 may also, or alternatively, be installed in and/or attached to housing 101. Additionally, or alternatively, electrical module 440 may output the electrical signal based on an instruction received from processing unit 200 and/or may output a signal to processing unit 200 indicating that the electrical signal has been output by electrical module 440.

FIGS. 8A-8D are diagrams of different types of example blink reflex responses 800-875, respectively, associated with a subject. Blink reflex responses 800-875 may be obtained, measured and/or generated by blink reflex device 100 and/or blink reflex devices 100-100 based on a blink reflex of a subject. As shown in FIGS. 8A-8D, blink reflex responses 800-875, respectively, may each include distance scale 655 and time scale 660 as described above with respect to FIG. 6C. Blink reflex responses 800-875 are shown in FIGS. 8A-8D, respectively, as corresponding to a single blink of the eye that occurs during a particular time period, for simplicity. In practice, blink reflex responses 800-875 may correspond to two or more blinks of the eye that occur over an extended period of time that is greater than that the particular time period.

Figures 8A, 8B:
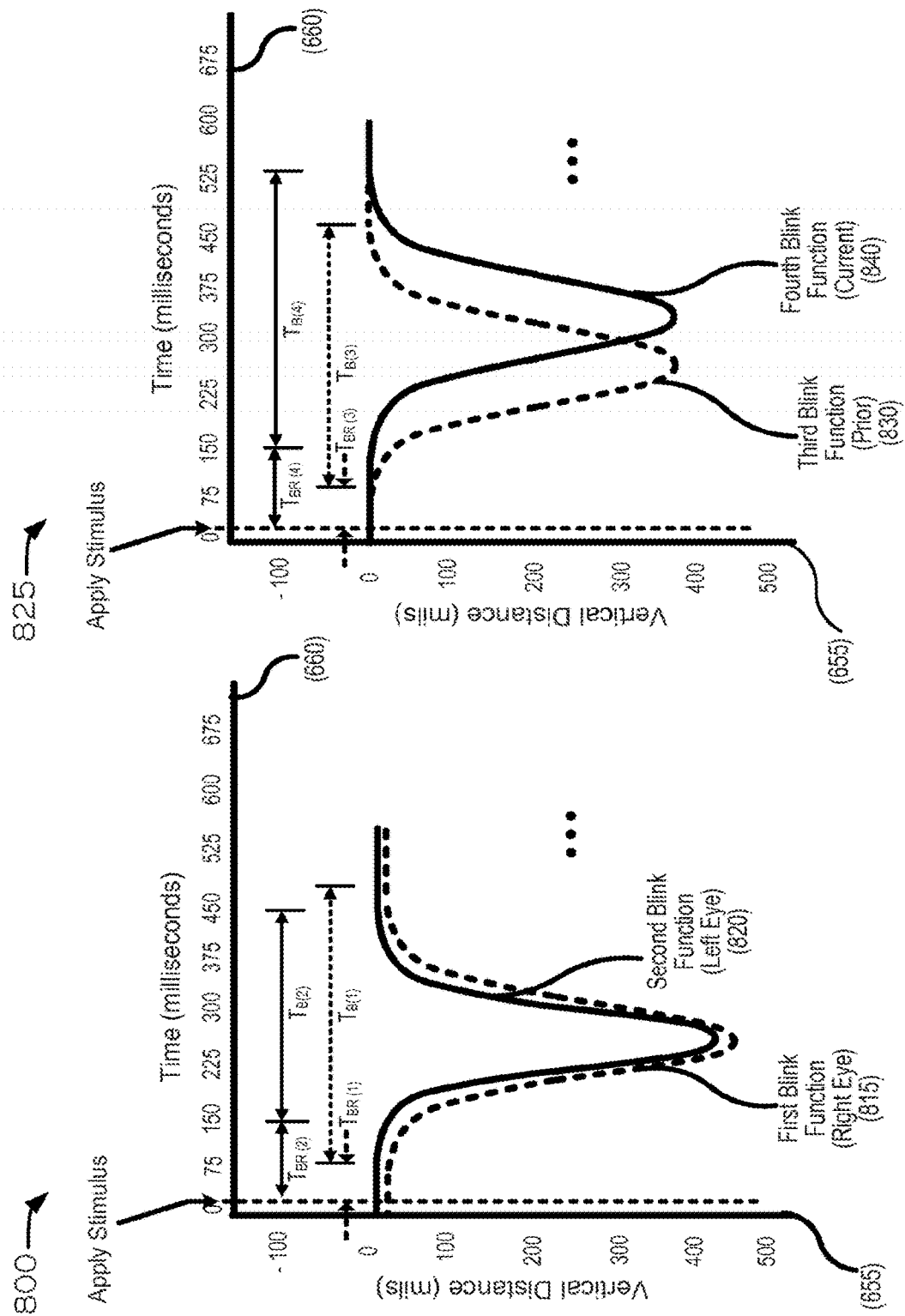
FIGS. 8A-8D are diagrams of different types of example blink reflex responses associated with a subject.

As shown in FIG. 8A, blink reflex response 800 (hereinafter "response 800") may include a first blink function 815 associated with the right eye and a second blink function 820 associated with the left eye. First blink functions 815 and second blink function 820 may, in a manner similar to that described above with respect to FIG. 6C, represent a blink reflex of the right eye and left eye of the subject, respectively, obtained by blink reflex device 100. Blink reflex device 100 may determine a first time period, associated with first blink function 815 that corresponds to a first blink reflex of the right eye (e.g., $T_{BR(1)}$). Blink reflex device 100 may determine a second time period, associated with second blink function 820 that corresponds to a second blink reflex of the left eye (e.g., $T_{BR(2)}$).

Additionally, or alternatively, blink reflex device 100 may apply stimulus (e.g., mechanical, optical, acoustic, electrical, etc.) to one eye and/or the proximity thereof (e.g., the right eye in our case) and may obtain a first blink reflex from the right eye (e.g., $T_{BR(1)}$) and a first blink reflex of the left eye (e.g., $T_{BR(2)}$) in response to the stimulus to the right eye. The right eye to which the stimulus is applied may sometimes be referred to herein as the "stimulated eye" or the "ipsilateral eye." The left eye, that did not receive the stimulus, may sometimes be referred to herein as the "non-stimulated eye" or the "contralateral eye." In such a case, there may be a period of delay between the initiation of the blink reflex of the ipsilateral eye relative to the other, contralateral eye. The period of delay may correspond to the difference in blink reflex between the ipsilateral eye and contralateral eye (e.g., $T_{BR(1)} < T_{BR(2)}$). Such a difference in blink reflex, between the ipsilateral eye and the contralateral eye, may be due to the additional neural pathways and/or distance that electrical brain signals must travel to trigger the blink reflex in the non-stimulated, contralateral eye (e.g., the left eye in our case). In the event that the difference in blink reflex between the ipsilateral eye and contralateral eye (e.g., $\Delta T_{BR} = |T_{BR(1)} - T_{BR(2)}|$) changes by more than a first threshold (e.g., after a traumatic event to the head or spine of the subject), such neural pathways may have been effected or impaired by the trauma or some neurological functional impairment.

Additionally, or alternatively, despite the larger blink reflex of the non-stimulated eye (e.g., the left eye), the first blink period of the non-stimulated eye (e.g., $T_{B(2)}$) may be less than the first blink period of the stimulated right eye (e.g., $T_{B(2)} < T_{B(1)}$, where $T_{B(1)}$ is the first blink period of the right eye). In the event that the difference in blink period between the ipsilateral eye and contralateral eye (e.g., $\Delta T_B = |T_{B(1)} - T_{B(2)}|$) changes by more than a second threshold (e.g., after a traumatic event to the head or spine of the subject), such neural pathways may have been effected or impaired by the trauma or some neurological functional impairment.

If, however, blink reflex device 100 applies stimuli to both eyes (e.g., either sequentially or at approximately the same time), the difference between the right eye blink reflex or blink period and the left eye blink reflex or blink period, respectively, may be an indication of a brain injury and/or a degenerative neurological condition associated with one or both sides of the brain and/or one or more neural pathways of the brain through which electrical brain signals that trigger the blink reflex travel.

As shown in FIG. 8B, blink reflex response 825 (hereinafter "response 825") may include a third blink function 830 and a fourth blink function 840. Third blink function 830 may, in a manner similar to that described above with respect to FIGS. 6B and 8A, represent a third blink reflex of an eye of the subject obtained, by blink reflex device 100, at a third point in time before the subject suffered from trauma or was known not to be suffering from a brain injury or degenerative neurological disorder) (sometimes referred to herein after "baseline blink reflex"). Additionally, or alternatively, third blink function 830 may represent a combination of third blink reflex functions (e.g., an average, a mean, a median, a weighted average, etc.) associated with one or more other subjects that are known not to suffer from a brain injury or degenerative neurological disorder. Such other subjects may, for example, be associated with one or more similar demographic parameters relative to the subject (e.g., similar age group, gender, race, etc.). Fourth blink function 840 may correspond to a fourth blink reflex of the eye obtained, by blink reflex device 100, at a fourth point in time that occurs at a current time and/or within a short time period after the subject is known to have suffered from trauma (e.g., within 5 minutes, 10 minutes, 30 minutes, 1 hour, 2 hours, 5 hours, 12 hours, 24 hours, etc.). Blink reflex device 100 may, based on third blink function 830, determine a third blink reflex of the eye (e.g., $T_{BR(3)}$) and/or, based on fourth blink function 840, determine a fourth blink reflex of the eye (e.g., $T_{BR(4)}$). In the event that the difference in baseline blink reflex and the post-trauma blink reflex (e.g., $\Delta T_{BR} = |T_{BR(3)} - T_{BR(4)}|$) changes by more than a third threshold, a potential brain injury or degenerative neurological condition may exists within the subject. Similarly, in the event that the difference between baseline blink period and the post-trauma blink period (e.g., (e.g., $\Delta T_B = T_{BR(3)} - T_{BR(4)}$ |) is greater than a fourth threshold, a potential brain injury or degenerative neurological condition may exists within the subject.

Figures 8C, 8D:
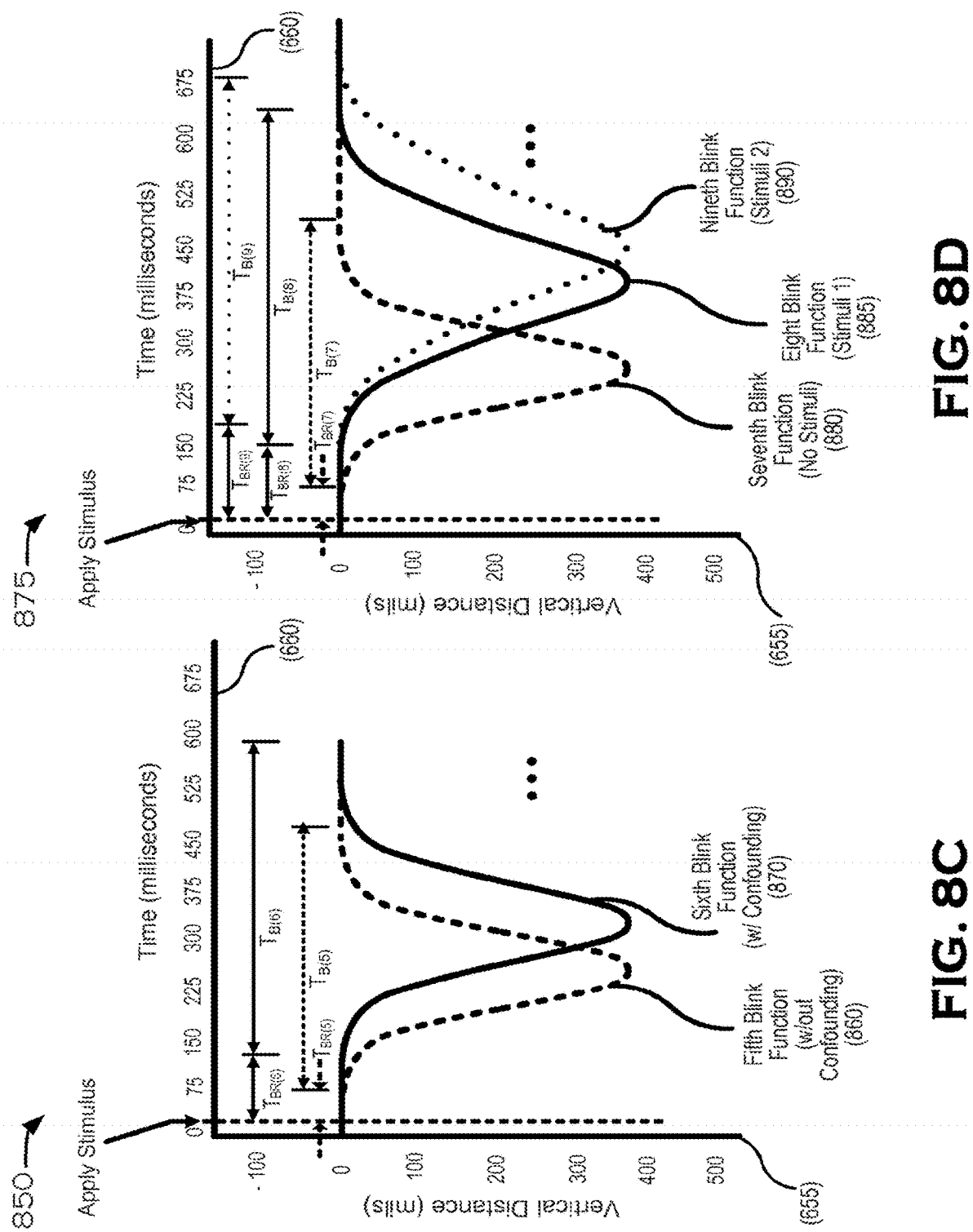

As shown in FIG. 8C, blink reflex response 860 (hereinafter "response 860") may include a fifth blink function 860 and a sixth blink function 870. Fifth blink function 860 may identify a fifth blink reflex and/or fifth blink period of an eye (e.g., the right or left eye) of the subject obtained without confounding the subject prior to and/or while applying stimuli to the subject. Sixth blink function 870 may identify a sixth blink reflex and/or a sixth blink period of the eye (e.g., the right or left eye) based on confounding the subject prior to and/or while applying the stimuli to the subject. As shown with respect to fifth blink function 860, blink reflex device 100 may determine the fifth blink reflex (e.g. $T_{BR(5)}$) and/or the fifth blink period (e.g., $T_{B(5)}$) of the eye without confounding. As shown with respect to sixth blink function 870, blink reflex device 100 may determine the sixth blink reflex (e.g., $T_{BR(6)}$) and/or the sixth blink period (e.g., $T_{B(6)}$) of the eye with confounding. Blink reflex device 100 may, in a manner to be described later, use differences between the fifth and sixth blink reflexes with and without confounding and/or differences in the fifth and sixth blink periods with and without confounding to determine whether a potential brain injury or degenerative neurological condition exists within the subject.

As shown in FIG. 8D, blink reflex response 875 (hereinafter "response 875") may include a seventh blink function 880, an eighth blink function 885, and a ninth blink function 890 obtained and/or created by blink reflex device 100. Seventh blink function 880 may identify a seventh blink reflex (e.g., $T_{BR(7)}$) and a seventh blink period (e.g., $T_{B(7)}$) of the eye of the subject (e.g., right or left eye) without providing any stimuli to the subject. Eighth blink function 885 may identify an eighth blink reflex (e.g., $T_{BR(8)}$) and an eighth blink period (e.g., $T_{B(8)}$) of the eye based on providing a first type of stimuli (e.g., mechanical, optical, acoustic, electrical, etc. stimuli) to the eye or proximity thereof of the subject. Ninth blink function 890 may identify a ninth blink reflex (e.g., $T_{BR(9)}$) and a ninth blink period (e.g., $T_{B(9)}$) of the eye based on applying a second, different type of stimuli to the subject. Blink reflex device 100 may, in a manner to be described below, use the differences in one or more of these blink reflex and between these blink periods to determine whether a potential brain injury or degenerative neurological condition exists within the subject.

Figure 9:
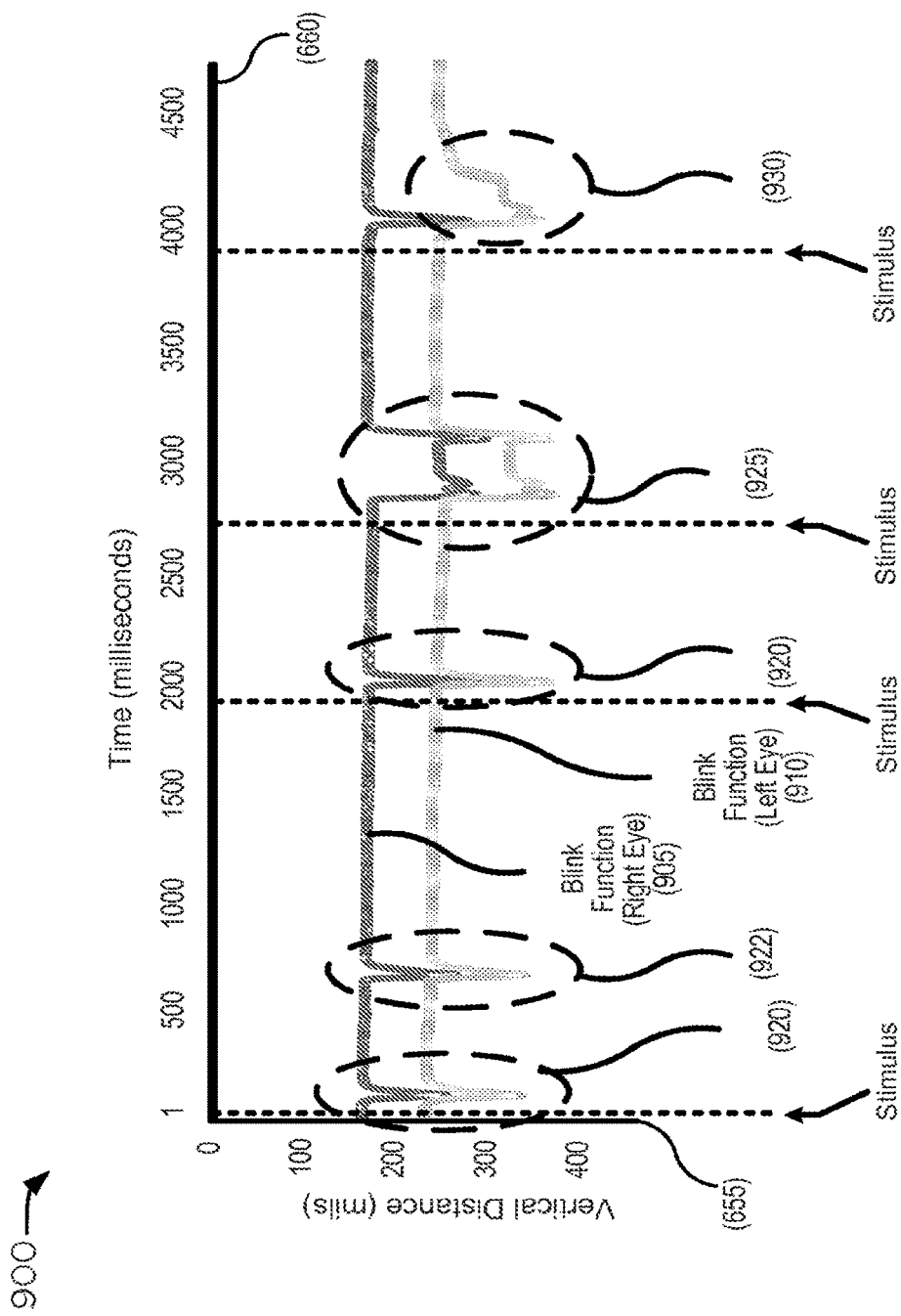
FIG. 9 is a diagram of an example blink reflex response, associated with a subject, that includes data to be removed and/or filtered from the example blink reflex response.

FIG. 9 is a diagram of an example blink reflex response 900 (hereinafter, "response 900"), associated with a subject that includes data to be removed and/or filtered from response 900. As shown in FIG. 9, response 900 may be created by blink reflex device 100 and/or blink reflex devices 100-100, based on multiple blinks of a right eye of a subject, associated with blink function 905 and multiple blinks of a left eye of the subject associated with blink function 910. In a manner similar to that described above with respect to FIGS. 8A-8D, a normal blink of the right and/or left eye may correspond to approximately symmetric peaks in portions of blink responses 905 and/or 910 (e.g., as shown by ellipses 920). Such peaks may correspond to a normal blink reflex in response to stimulus being provided to the subject and/or a normal blink period based on stages A through G (FIG. 6B) in which the eye begins in the open state (e.g., stage A in which the eyelids are in an initial position), transitions to the closed state (e.g., stage D) and returns to the open state (e.g., stage G in which the eyelids return to approximately the initial position of stage A). Additionally, blink responses 905 and/or 910 may include a normal blink reflex and/or blink period that is voluntary or spontaneous that is not in response to any stimulus being provided to the subject (e.g., as shown by ellipse 922).

Additionally, or alternatively, blink reflex device 100 may detect a blink that is not a normal blink (sometimes referred to as a "double blink") in which one or both eyes transition from the open state to the close state and begin returning to the open state, but reverse direction and begin closing and/or returning to the closed state prior to reaching the open state (e.g., as shown by ellipse 925). Additionally, or alternatively, blink reflex device 100 may detect a blink that is not a normal blink (sometimes referred to as a "micro-sleep") in which one or both eyes transition from the open state to the close state and begin returning to the open state at rate that is substantially slower than that associated with a normal blink. Such a double blink and/or micro-sleep event may be an indication that the subject is experiencing fatigue and/or may occur over a prolonged period that is substantially longer than the normal blink reflex (e.g., 5 times longer, 10 times longer, 20 times longer). Such data could be used, by blink reflex device 100 to identify potential impairments in cognitive alertness of the subject and/or to determine whether a potential brain injury or degenerative neurological condition exists within the subject. Additionally, or alternatively, for determining a blink reflex and/or blink period, data associated with a double blink and/or micro-sleep event may introduce errors into the determination of the period of time during which a blink reflex occurs. Blink reflex device 100 may reject, discard, or ignore such data when determining the blink reflex and/or blink period.

Figure 10:
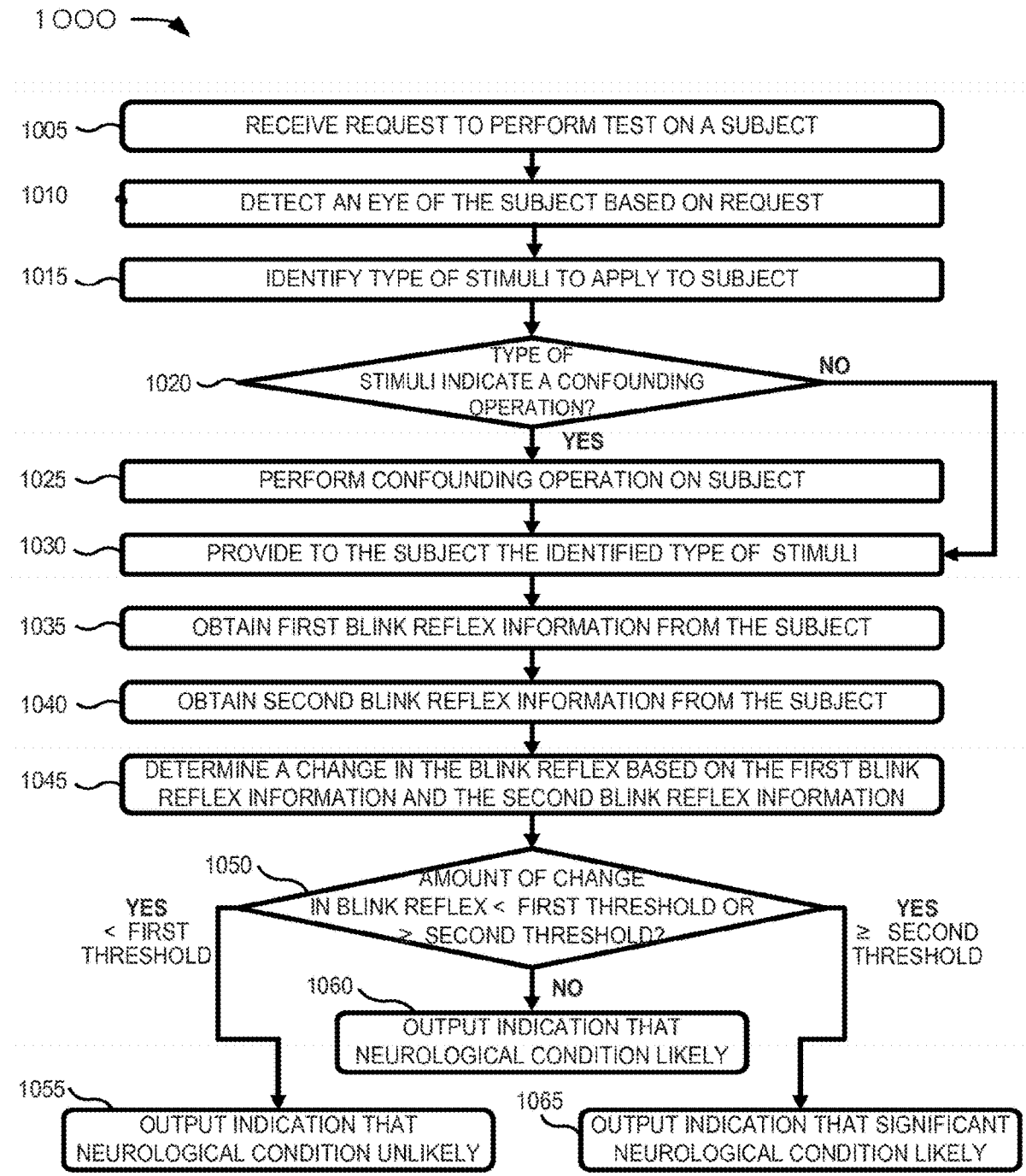
FIG. 10 is a flowchart of an example process for determining whether a subject suffers from brain injury or a degenerative neurological condition.
Figure 11:
FIG. 11 is a diagram of an example data structure that may store information associated with a blink reflex of a subject.

FIG. 10 is a flowchart of an example process 1000 for determining whether a subject suffers from brain injury or a degenerative neurological condition. Process 1000 may be performed by one or more devices associated with blink reflex device 100 and/or 100-100. Additionally, or alternatively, some or all of process 1000 may be performed by a device, or collection of devices separate from, or in combination with blink reflex device 100 and/or 100-100. FIG. 11 is a diagram of an example data structure 1100 that may store information associated with a blink reflex of a subject. FIG. 12 is a diagram of an example data structure 1200 that stores information associated with a change in blink reflex of a subject. Process 1000 of FIG. 10 will be described with references to all or a portion of data structure 1100 of FIG. 11 and data structure 1200 of FIG. 12.

In the description below, assume that a subject has been subject to a traumatic event, such as, for example, a blow to the head that a player in an athletic event might experience during a game (e.g., a football player, soccer player, lacrosse player, etc.), a driver of a car might experience during an accident, etc. Assume further that a user (e.g., a coach, a paramedic, a nurse, etc.), associated with blink reflex device 100, places blink reflex device 100 on the subject in a manner that enables blink reflex device 100 to obtain (e.g., detect, measure, record, etc.) a blink reflex response associated with the subject.

As shown in FIG. 10, process 1000 may include receiving a request to perform a test on a subject (block 1005) and detect an eye of the subject based on the request (block 1010). For example, blink reflex device 100 may receive an instruction to obtain a blink reflex response from the subject, such as when the user selects a particular button (e.g., to power up blink reflex device 100, etc.) on blink reflex device 100 and/or when blink reflex device 100 is placed on the subject, etc.). Blink reflex device 100 (e.g., sensor unit 215)

may, based on receiving the instruction, may detect one or both eyes of the subject. For example, blink reflex device 100 may receive information associated with the eye of the subject (e.g., the face, one or both eyes, one or more eyelids, an area around an eye, etc. of the subject) and may determine whether the received information matches stored information (e.g., a visual signature of a standard eye stored in memory 210) associated a particular eye, such as a video and/or image of a standard eye, eyelid, proximity thereof. In the event that the received information matches the stored information, blink reflex device 100 may use one or more known techniques to create a corneal reflection (e.g., corneal reflection 515 of FIG. 6A) on and/or within the eye to identify one or more tracking points associated with the subject (e.g., upper eyelid tracking point 525 (FIG. 6A), lower eye tracking point 530 (FIG. 6A), and/or some combination of upper and/or lower eyelid tracking points). Blink reflex device 100 may also, or alternatively, identify an initial location of the upper eyelid (e.g., based on upper eyelid tracking point 525) and/or the lower eyelid (e.g., based on lower eyelid tracking point 530) when the eye is in the open state. Blink reflex device 100 may output a notification that a tracking point has been identified. In the event that the received information does not match the stored information, blink reflex may output a notification that alerts the user that a tracking point cannot be identified.

As also shown in FIG. 10, process 1000 may include identifying a type of stimuli to apply to the subject (block 1015). For example, blink reflex device 100 may, based on identifying a tracking point associated with the eye, determine a type of stimuli that is to be used to obtain a blink reflex response from the subject. Blink reflex device 100 may, for example, receive an indication from the user that identifies the type of stimuli when the user selects a particular button on blink reflex device 100 (e.g., a button identifying mechanical, optical, acoustic, and/or electrical stimuli). Additionally, or alternatively, a particular type of stimuli, such as, for example, a mechanical stimuli (e.g., a puff of fluid, a pin prick, etc.) may be pre-programmed (e.g., as a default stimuli) into blink reflex device 100 by the user or during manufacturing. Blink reflex device 100 may also, or alternatively, receive an indication from the user (e.g., by selecting a specific button, preprogramming by user, preprogramming during manufacture, etc.) whether stimuli is to be provided to the right eye and/or proximity thereof, the left eye and/or proximity thereof, and/or both eyes and/or proximities thereof.

Additionally, or alternatively, the user may indicate whether a confounding operation is to be performed on the subject by selecting a certain button on blink reflex device 100. Blink reflex device 100 may include a default mode (e.g., preprogrammed by the user and/or during manufacturing) that does not include a confounding operation.

As further shown in FIG. 10, if the type of stimuli indicates a confounding operation (block 1020—YES), process 1000 may include performing a confounding operation on the subject (block 1025). For example, blink reflex device 100 may determine that a confounding operation is to be performed and may (e.g., using stimulator 102, confounder module 450, etc.) perform a confounding operation on the subject. The confounding operation may cause the subject respond to questions, audible sounds, a flash of light, etc. for the purpose of distracting the subject, which may preclude the subject from anticipating the stimuli and/or avoiding the surprise of the stimuli. Being surprised and/or startled by the stimuli may cause the subject to blink as a reflex in response to the stimuli rather than in anticipation of such stimuli, which may lead to inaccurate results. For example, blink reflex device 100 may perform the confounding operation by intermittently displaying one or more lights in the field of view of the subject and blink reflex device 100 and/or the user may direct the subject to identify when one of the lights is lit and/or the position of each light within the field of view. The confounding operation may cause the subject to focus concentration on one or more of the intermittent lights, which may preclude the subject from anticipating the stimuli. Additionally, or alternatively, blink reflex device 100 may also, or alternatively, perform the confounding operation using one or more sounds in which blink reflex device 100 and/or the user directs the subject to identify when a sound is made, which ear the sound is directed, whether the pitch is increasing or decreasing, etc. Blink reflex device 100 may also, or alternatively, perform other confounding operations (e.g., mechanical, electrical, etc.) by causing, for example, the subject to interact with a user interface displayed on user device 110 and/or blink reflex device 100 by answering questions, pointing to moving targets, etc.

As yet further shown in FIG. 10, if the type of stimuli does not indicate a confounding operation (block 1020—NO) or while performing the confounding operation on the subject (block 1025), process 1000 may include providing to the subject the stimuli based on the identified type of stimuli (block 1030). For example, blink reflex device 100 may determine that the identified type of stimuli indicates that a confounding operation is not to be performed on the subject. Blink reflex device 100 may, based on the determination that the confounding operation is not to be performed, provide the stimuli to the subject without performing the confounding operation. Alternatively, blink reflex device 100 may, while performing the confounding operation in a manner described above with respect to block 1025, provide stimuli to the subject while the confounding operation is being performed.

For example, blink reflex device 100 may provide a stimulus to the subject to cause the subject to reflexively blink in a manner that can be detected, monitored and/or recorded by blink reflex device 100. Additionally, or alternatively, blink reflex device 100 may stimulate the subject based on the identified type of stimuli. For example, if the type of stimuli corresponds to a mechanical stimulation, blink reflex device 100 (e.g., stimulator 102, mechanical module 410, etc.) may cause a puff of fluid (e.g., air, nitrogen, water, water vapor, etc.) to be directed and/or targeted to the selected eye of the subject (e.g., selected by the user and/or based on preprogramming). The puff of fluid may be associated with a particular volume, direction, pressure, velocity, acceleration, force, etc. that causes the subject to be startled or surprised. Additionally, or alternatively, if the type of stimuli corresponds to an optical stimulation, blink reflex device 100 (e.g., stimulator 102, light module 420, etc.) may cause a beam of light to be shined in the selected eye of the subject. The beam of light may be associated with a particular intensity, power, frequency, beam width, etc. that causes the subject to be startled or surprised.

Additionally, or alternatively, if the type of stimuli corresponds to an acoustic stimulation, blink reflex device 100 (e.g., stimulator 102, acoustic module 430, etc.) may cause a sound (e.g., a loud tone, music, etc.) to be directed into an ear, of the subject, that corresponds to the same side of the subject as the selected eye of the subject. The sound may be associated with a volume level, power level, frequency range, directivity, etc. that causes the subject to be startled or surprised. Additionally, or alternatively, if the type of stimuli corresponds to an electrical stimulation, blink reflex device 100 (e.g., stimulator 102, electrical module 420, etc.) may cause a beam of light to be shined in the selected eye of the subject. The beam of light may be associated with a particular intensity, power, frequency, beam width, etc. that causes the subject to be startled or surprised.

As also shown in FIG. 10, process 1000 may include obtaining first blink reflex information from the subject (block 1035) and obtaining second blink reflex information from the subject (block 1040). For example, blink reflex device 100 may, at a first time, track the manner in which the subject reflexively blinks as a result of providing the stimuli to the subject. The first time (e.g., T1) may correspond to a time during or after which the subject experiences a traumatic event associated with a blow or impact to the head. Blink reflex device 100 may track and/or record, as a function of time, the location along blink axis 520 (FIG. 6A) of one or more upper eyelid tracking points 525, lower eyelid tracking points 530 and/or some other tracking points relative to the initial location of such tracking points (e.g., when the eye is in the open state) to obtain information associated with the first blink reflex of the subject (sometimes referred to a "blink function") in a manner similar to that described above with respect to FIGS. 6B and 8A-8D. Additionally, or alternatively, blink reflex device 100 may identify certain abnormal blink functions, such as a micro-blink and/or double-blink in a manner similar to that described above with respect to FIG. 9 and may discard, ignore, or erase a portion of the information associated with the first blink reflex to which the abnormal blink corresponds. Additionally, or alternatively, blink reflex device 100 may determine whether the subject potentially suffers from fatigue, cognitive impairment and/or impaired neurological function based on the information associated with the abnormal blink functions.

Additionally, or alternatively, blink reflex device 100 may obtain information associated with the blink of the subject when stimuli has not been provided to the subject, such as when the subject intentionally blinks (e.g., in response to a command from the user) and/or when the subject naturally blinks to lubricate the surface of the eye. Blink reflex device 100 may also, or alternatively, store the information, associated with the first blink reflex and/or first blink period, in a data structure (e.g., data structure 1100 of FIG. 11 to be described below) within a memory associated with blink reflex device 100 (e.g., memory 210) and/or may transmit the information, associated with first blink reflex and/or first blink period, to server 120 and/or database 130 for storage in a data structure.

Additionally, blink reflex device 100 may retrieve from a memory (e.g., memory 210), database 130 and/or server 120, information associated with a second blink reflex obtained at a prior, second point in time (e.g., T2). The information associated with the second blink reflex may have been obtained from the subject at the second time before the subject experienced the traumatic event and/or when the subject is known not to be suffering from a neurological condition. Additionally, or alternatively, the information, associated with the second blink reflex and/or second blink period, may correspond to a combination of one or more blink functions (e.g., an average, mean, median, etc.) of one or more other subjects (e.g., of the same or similar demographics, such as age, race, gender, etc. relative to the subject) at the second time when the other subjects are known not to be suffering from a neurological condition.

For example, as shown in FIG. 11, data structure 1100 may store information associated with the blink reflex of a subject and/or other subjects and may include a collection of fields, such as a subject info field 1105, a stimuli type field 1110, a confound field 1115, an eye identifier field 1120, a baseline time field 1100, a baseline blink reflex field 1130, a time field 1135, and a blink reflex field 1140. Additionally, or alternatively, data structure 1100 may be stored by blink reflex device 100 (e.g., memory 210), server 120, and/or database 130. The number of fields illustrated in FIG. 11, is provided for explanatory purposes only. In practice, there may be additional fields; fewer fields; different fields; or differently arranged fields than illustrated in FIG. 11.

Fields 1105 through 1130 may, for example, correspond to information previously obtained from the subject or other subjects prior to a traumatic event experienced by the subject. The other subjects may be associated with similar parameters or demographics as the subject (e.g., similar age, race, gender, size, weight, etc.). Fields 1135 and 114 may correspond to information obtained from the subject after the traumatic event is experienced by the subject. Subject info field 1105 may store information associated with a subject from which information associated with the first blink reflex and/or second blink reflex is obtained. For example, information, associated with the subject, may identify a name of the subject, an address of the subject, demographic information associated with the subject (e.g., age, gender, race, etc.), prior history (e.g., prior incidences of brain injury, neurological impairment, etc.), a unique identifier associated with the subject (e.g., a number, string, all or a portion of a social security number, etc.), etc. Subject info field 1105 may also, or alternatively, store information associated with one or more other subjects, known not to be suffering from a neurological condition, from which respective information, associated with a second blink reflex, is obtained. Additionally, or alternatively, the demographic information, associated with the other subjects, may be the same or similar to that of the subject.

Stimuli type field 1110 may store information that identifies a type of stimuli used to obtain the information associated with the first blink reflex or the second blink reflex. For example, the information that identifies the type of stimuli may identify if no stimuli was used (e.g., shown as S0 within stimuli type field 1110 of FIG. 11) or whether mechanical stimuli (e.g., shown as S1 within stimuli type field 1110 of FIG. 11), light stimuli (e.g., shown as S2 within stimuli type field 1110 of FIG. 11), acoustic stimuli (e.g., shown as S3 within stimuli type field 1110 of FIG. 11), and/or electrical stimuli (e.g., shown as S4 within stimuli type field 1110 of FIG. 11) was used to obtain the information associated with the first blink reflex and/or second blink reflex. Stimuli type field 1110 may also, or alternatively, store information that identifies whether the stimuli is provided to the left eye, right eye, both eyes or proximity thereof of the subject.

Confound field 1115 may store information that identifies whether a confounding operation was performed on the subject to obtain the information associated with the first blink reflex or the second blink reflex (e.g., shown as C0 in field 1115 of FIG. 11 if a confounding operation was not performed, and C1 if a confounding operation was performed). Eye identifier field 1120 may store information that identifies whether the information associated with the first blink reflex or second blink reflex was obtained from the subject with respect to the left eye (e.g., shown as L within stimuli type field 1120 of FIG. 11), right eye (e.g., shown as R within stimuli type field 1120 of FIG. 11) or both eyes (e.g., shown as B within stimuli type field 1120 of FIG. 11). Baseline time field 1100 may store information (e.g., a date, time, etc.) that identifies a previous time (e.g., identified above as the second time and shown as T2 within baseline time field 1100 of FIG. 11) at which a blink reflex operation was performed (e.g., by blink reflex device 100) to obtain the information associated with the second blink reflex or second blink period of the subject or one or more other subject (e.g., other subjects associated with the same or similar demographics as the subject). The previous time may, for example, correspond to a time before the subject experienced a traumatic event and/or when it is known that the subject or the other subjects are known not to be suffering from a neurological condition. Baseline blink reflex field 1130 may store information associated with the second blink reflex and/or second blink period. The information associated with the second blink reflex and/or second blink period may, in a manner similar to that described above with respect to FIGS. 6B and 8A-8D, correspond to a blink function of the subject.

Time field 1135 may store information (e.g., a date, time, etc.) that identifies a time (e.g., identified above as the first time or a current time and shown as T1 in time field 1135 of FIG. 11) at which a blink reflex operation was performed (e.g., by blink reflex device 100) to obtain the information associated with the first blink reflex and/or first blink period of the subject. The time may, for example, correspond to a particular time during or after which the subject experiences a traumatic event and/or when it is known that the subject is suffering from a neurological condition. Blink reflex field 1140 may store information associated with the first blink reflex and/or the first blink period of the subject. The information associated with the first blink reflex and/or first blink period may, in a manner similar to that described above with respect to FIGS. 6B and 8A-8D, correspond to a blink function of the subject that identifies a vertical distance that one or more eyelids, of the subject, move during one or more blinks by the subject as a function of time during which the one or more blinks are measured.

By way of an example associated with dashed ellipse 1152 of FIG. 11, at the second time (e.g., T2), blink reflex device 100 may have previously obtained information associated with the second blink reflex and/or second blink response of the subject without stimuli to the subject (e.g., S0), without performing a confounding operation (e.g., NC), and/or from both eyes of the subject (e.g., B) and may store such information in data structure 1100 (e.g., shown as BTB0).

Additionally, or alternatively, at the first time (e.g., T1) that occurs after the second time (e.g., T2) and after the subject has experienced a traumatic event or is known to suffer from a degenerative neurological condition, blink reflex device 100 may obtain information associated with the first blink reflex and/or first blink period of the subject under the same conditions as described in the previous paragraph. Blink reflex device 100 may store such information in data structure 1100 (e.g., shown as BT0).

Additionally, or alternatively, as shown with respect to dashed ellipse 1154 of FIG. 11, information associated with the second blink reflex and/or second blink period of the subject, may have been previously obtained at the second time (e.g., T2) under the same conditions as those described above, except in this case the subject was being confounded by blink reflex device 100 (e.g., shown as C in confound field 1115). Blink reflex device 100 may, in this example, store the information associated with second blink reflex in data structure 1100 (e.g., shown as BTB1). Blink reflex device 100 may, during the first time (e.g., T1), obtain information associated with the first blink reflex and/or the first blink period under the confounding conditions described in this example, and may store such information in data structure 1100 (e.g., shown as BT1).

Additionally, or alternatively, as shown with respect to dashed ellipse 1156 of FIG. 11, at the second time (e.g., T2), blink reflex device 100 may have previously obtained information associated with the second blink reflex and/or second blink period in one or more separate measurements of the right eye (e.g., shown as R) and of the left eye of the subject (e.g., shown as L), by providing a first stimuli to the subject (e.g., a mechanical stimuli shown as S1), and performing a confounding operation on the subject (e.g., shown as C). Blink reflex device 100 and may store such information in data structure 1100 (e.g., shown as RTB1 for the right eye and LBT1 for the left eye). Additionally, or alternatively, at the first time (e.g., T1) that occurs after the second time and after the subject has experienced a traumatic event or is known to suffer from a degenerative neurological condition, blink reflex device 100 may obtain information associated with the first blink reflex and/or first blink period of the subject (e.g., for the right eye and separately for the left eye) under the same conditions as described immediately above and may store such information in data structure 1100 (e.g., shown as RT1 for the right eye and LT1 for the left eye).

Additionally, or alternatively, as shown with respect to dashed ellipse 1158, blink reflex device 100 may, at the second time (e.g., T2), have previously obtained information associated with second blink reflex and/or second blink period from the right and/or left eye based on the conditions set forth in the previous example with respect to dashed ellipse 1156, except that no confounding operation is performed (e.g., NC). Blink reflex device 100 may store such information in data structure 1100 (e.g., shown as RTB2 for the right eye and LTB2 for the left eye). Additionally, or alternatively, blink reflex device 100 may, at the first time (e.g., T1), obtain information associated with the first blink reflex and/or first blink period of the subject under the same conditions as described immediately above and may store such information in data structure 1100 (e.g., shown as RT2 for the right eye and LT2 for the left eye). Blink reflex may also, or alternatively, have previously obtained (e.g., at T1) and/or may obtain (e.g., at T2) other information associated with the first blink reflex/first blink period or the second blink reflex/second blink period based on other types of stimuli (e.g., shown as S2, S3, S4, etc.) and may store such information in data structure 1100 (e.g., as shown by dashed rectangle 1160 of FIG. 1100).

Returning to FIG. 10, process 1000 may include determining a change in the blink reflex based on the first blink reflex information and the second blink reflex information (block 1045). For example, blink reflex device 100 (e.g., processing unit 200) may compare the information associated with the first blink reflex and/or first blink period of the subject with the information associated with the second blink reflex and/or second blink period. The information may be associated with the second blink reflex or second blink period may have been obtained from the subject and/or one or more other subjects. In the latter case, the information associated with the second blink reflex and/or second blink period may be based on a combination of information taken from one or more second blink reflexes and/or second blink periods of one or more other subjects (e.g., based on an average, mean, median, etc.), obtained under the same and/or similar conditions (e.g., type of stimuli, with or without confounding, etc.). Blink reflex device 100 may identify an amount of difference or change between the information associated with the first blink reflex and/or blink period and the information associated with the second blink reflex and/or blink period. For example, blink reflex device 100 may, with respect to conditions in which the subject is not stimulated or confounded, compare the information associated with the first blink reflex or blink period of the subject (e.g., BT0 in the case of both eyes being measured) with the information associated with the second blink reflex and/or blink period (e.g., BTB0), to identify an amount of change or difference in the blink reflex and/or blink period under such conditions (e.g., $\Delta B0=|BT0-BTB0|$). Additionally, or alternatively, blink reflex device 100 may, with respect to conditions in which the subject is not stimulated but is confounded, compare the information associated with the first blink reflex and/or first blink period of the subject (e.g., BT1) with the information associated with the second blink reflex and/or second blink period (e.g., BTB1), to identify an amount of change in the blink reflex and/or blink period (e.g., $\Delta B1$) under such conditions (e.g., $\Delta B1=|BT1-BTB1|$).

Additionally, or alternatively, blink reflex device 100 may, with respect to conditions in which the subject is being stimulated (e.g., using mechanical stimulation) and is being confounded, compare the information associated with the first blink reflex and/or blink period of the subject (e.g., RT1 in the case of the right eye) with the information associated with the second blink reflex and/or blink period (e.g., RTB1), to identify an amount of change in the blink reflex and/or blink period of the right eye under such conditions (e.g., $\Delta R1=|RT1-RTB1|$). Additionally, or alternatively, blink reflex device 100 may, with respect to conditions in which the subject is stimulated (e.g., using mechanical stimulation) but is not confounded, compare the information associated with the first blink reflex and/or blink period of the subject (e.g., RT2 in the case of the right eye) with the information associated with the second blink reflex and/or blink period (e.g., RTB2), to identify an amount of change in the blink reflex and/or blink period of the right eye under such conditions (e.g., $\Delta R2=|RT2-RTB2|$).

Blink reflex device 100 may perform a similar comparison for the right eye, left eye and/or both eyes for other conditions associated with different types of stimuli (e.g., light, acoustic, electrical, etc.) with and/or without confounding the subject and may determine the amount of change or difference in the blink reflex and/or blink period of the subject.

Additionally, or alternatively, blink reflex device 100 may, under certain conditions, compare information associated with the first blink reflex or blink period for the right eye with information associated with the first blink reflex and/or blink period for the left eye to identify any asymmetry in such first blink reflexes. For example, blink reflex device 100 may, with respect to conditions in which the subject is stimulated (e.g., using mechanical stimulation) and is confounded, compare the information associated with the first blink reflex and/or blink period for the right eye (e.g., RT1) with the information associated with the first blink reflex and/or blink period for the left eye (e.g., LT1) to identify an amount of difference in the first blink reflex and/or blink period of the right eye relative to that of the left eye (e.g., $\Delta LR1$) under such conditions (e.g., $\Delta LR1=|RT1-LT1|$). Blink reflex device 100 may perform a similar comparison for other conditions associated with different types of stimuli (e.g., light, acoustic, electrical, etc.) with or without confounding the subject and may determine the amounts of difference in the first blink reflex between the ipsilateral eye and contralateral eyes of the subject. Additionally, or alternatively, blink reflex device 100 may store one or more values, associated with the change in blink reflex and/or blink period in first blink reflex in data structure 1100 of FIG. 11.

As shown in FIG. 10, if the amount of change or difference in the blink reflex is less than a first threshold, and not greater than or equal to a second threshold (block 1050— YES<FIRST THRESHOLD), process 1000 may include outputting an indication that brain injury is unlikely (block 1055). For example, blink reflex device 100 may determine whether the amount of change in the blink reflex and/or blink period, of the subject, before and after the subject experiences trauma (e.g., a blow to the head, etc.) is less than a first threshold. In the event that the amount of change is less than the first threshold, blink reflex device 100 may output an indication that it is unlikely that the subject suffers from a neurological condition. Such an indication may enable the user, of blink reflex device 100, to decide to allow the subject to resume normal activity, such as, for example, return to the playing field, operate an automobile, return to work, etc.

For example, blink device 100 may retrieve, from a data structure (e.g., data structure 1200 of FIG. 12) within a memory associated with blink reflex device 100, server 120, and/or database 130, information identifies one or more thresholds, associated with conditions under which information associated with a blink reflex is obtained from a subject. The thresholds may be used by blink reflex device 100 to determine if the subject suffers from a neurological condition and/or the severity thereof. As shown in FIG. 12, data structure 1200 may include a collection of fields such as a no impairment field 1210, and some impairment field 1215, and a significant impairment field 1220. The number of fields illustrated in FIG. 12, is provided for explanatory purposes only. In practice, there may be additional fields; fewer fields; different fields; or differently arranged fields than illustrated in FIG. 12.

No impairment field 1210 may store information that identifies a first threshold (e.g., shown as br1, nbr1, c1, nc1, clr1, cnlr1, etc. in FIG. 12) that corresponds to a time period, associated with a change in blink reflex and/or blink period, below which would indicate that the subject does not suffer from a neurological condition. For example, if the change in blink reflex of the subject is less than a first threshold for the conditions measured by blink reflex device 100, blink reflex device 100 may determine that it is not likely that the subject is suffering from a brain injury or degenerative neurological impairment.

Some impairment field 1215 may store information that identifies a range of time, from a first threshold to a second threshold (e.g., shown as br2, nbr2, c1, nc2, clr2, cnlr2, etc. in FIG. 12), associated with a change in blink reflex and/or blink period, within which would indicate that the subject is suffering from a neurological condition. The second threshold may be greater than the first threshold. For example, if the change in blink reflex of the subject is not less than a first threshold and is less than a second threshold for the conditions measured by blink reflex device 100, blink reflex device 100 may determine that it is likely that the subject is suffering from a brain injury or degenerative neurological impairment.

Significant impairment field 1220 may store information that identifies the second threshold that corresponds to a time period, associated with a change in blink reflex and/or blink period, above which would indicate that the subject is suffering from a significant brain injury or degenerative neurological condition. For example, if the change in blink reflex of the subject is not less than a second threshold, blink reflex device 100 may determine that it is likely that the subject is suffering from a significant neurological condition.

Returning to FIG. 10 and by way of example, with respect to conditions in which the subject is not stimulated or confounded, blink reflex device 100 may determine whether the amount of change in blink reflex and/or blink period (e.g., $\Delta B0$) is less than a first threshold (e.g., br1) associated with such conditions (e.g., shown as $\Delta B0 < br1$ in no impairment field 1210 of FIG. 12), where br1 represents the first threshold for conditions in which the subject is not stimulated or confounded). In the event that the amount of change is less than the first threshold, blink reflex device 100 may output an indication that it is unlikely that the subject suffers from a neurological condition. Additionally, or alternatively, with respect to conditions in which the subject is not stimulated but is confounded, blink reflex device 100 may determine whether the amount of change in blink reflex and/or blink period (e.g., $\Delta B1$) is less than a first threshold associated with such conditions (e.g., shown as $\Delta B1 < nbr1$ in no impairment field 1210 of FIG. 12, where nbr1 represents the first threshold for conditions in which the subject is not stimulated but is confounded).

Additionally, or alternatively, with respect to conditions in which the subject is stimulated and confounded, blink reflex device 100 may determine whether the amount of change in blink reflex and/or blink period (e.g., $\Delta R1$ for the right eye or $\Delta L1$ for the left eye) is less than a first threshold associated with such conditions (e.g., shown as $\Delta R1 < c1$ or $\Delta L1 < c1$ in no impairment field 1210 of FIG. 12, where c1 represents the first threshold for conditions in which the subject is stimulated and confounded). The change in blink reflex and/or blink period for conditions associated with other types of stimuli (e.g., light, acoustic, electrical, etc.) and confounding may be compared, in the manner described above, to other first thresholds for such conditions associated with the other types of stimuli and confounding.

Additionally, or alternatively, with respect to conditions in which the subject is stimulated but not confounded, blink reflex device 100 may determine whether the amount of change in blink reflex and/or blink period (e.g., $\Delta R2$ for the right eye or $\Delta L2$ for the left eye) is less than a first threshold associated with such conditions (e.g., shown as $\Delta R2 < nc1$ or $\Delta L2 < nc1$ in no impairment field 1210 of FIG. 12, where nc1 represents the first threshold for conditions in which the subject is stimulated but not confounded). The change in blink reflex and/or blink period for conditions associated with other types of stimuli (e.g., light, acoustic, electrical, etc.) but no confounding may be compared, in the manner described above, to other first thresholds for such conditions associated with the other types of stimuli and no confounding.

Additionally, or alternatively, with respect to conditions in which the subject is stimulated and confounded, blink reflex device 100 may determine whether the amount of difference between the first blink reflex and/or blink period of the ipsilateral and contralateral eye (e.g., $\Delta LR1$) is less than a first threshold associated with such conditions (e.g., shown as $\Delta LR1 < clr1$ in no impairment field 1210 of FIG. 12, where clr1 may represent the first threshold for conditions in which the subject is stimulated and confounded). The change in the first blink reflex between the ipsilateral and contralateral eye for conditions associated with other types of stimuli (e.g., light, acoustic, electrical, etc.) and confounding may be compared, in the manner described above, to other first thresholds for such conditions associated with the other types of stimuli and confounding. Additionally, or alternatively, with respect to conditions in which the subject is stimulated but not confounded, blink reflex device 100 may determine whether the amount of difference between the first blink reflex and/or blink period of the ipsilateral and contralateral eye (e.g., $\Delta LR2$) is less than a first threshold associated with such conditions (e.g., shown as $\Delta LR2 < nclr1$ in no impairment field 1210 of FIG. 12, where nclr1 may represent the first threshold for conditions in which the subject is stimulated but not confounded).

The change in the first blink reflex between the ipsilateral and contralateral eye for conditions associated with other types of stimuli (e.g., light, acoustic, electrical, etc.) and confounding may be compared, in the manner described above, to other first thresholds for such conditions associated with the other types of stimuli and confounding. In the event that each of the amounts of change in blink reflex and/or blink period are less than the respective first thresholds as described above, blink reflex device 100 may output an indication that it is unlikely that the subject suffers from a neurological condition. Additionally, or alternatively, if the difference in first blink reflex, between the ipsilateral and contralateral eye, is less than the corresponding first threshold, blink reflex device 100 may output an indication that it is unlikely that the subject suffers from a neurological condition.

As also shown in FIG. 10, if the change in the blink reflex is not less than the first threshold or not greater than or equal to the second threshold (block 1050—NO), process 1000 may include outputting an indication that brain injury is likely (block 1060). For example, blink reflex device 100 may determine whether the amount of change in the blink reflex and/or blink period, of the subject, before and after the subject experiences trauma indicates that the subject has suffered a brain injury and/or a degenerative neurological condition. Based on a determination that the subject suffers from a brain injury and/or a degenerative neurological condition, blink reflex device 100 may output an indication that it is likely that the subject suffers from a neurological condition. Such an indication may enable the user, of blink reflex device 100, to decide to prohibit the subject from resuming normal activity, such as, for example, prohibiting a subject from returning to the playing field, operating an automobile, returning to work, etc.

For example, with respect to conditions in which the subject is not stimulated or confounded, blink reflex device 100 may determine whether the amount of change in blink reflex and/or blink period (e.g., $\Delta B0$) is not less than the first threshold (e.g., br1) associated with such conditions and is not greater than or equal to a second threshold associated with such conditions (e.g., shown as $br1 \leq \Delta B0 < br2$ in some impairment field 1215 of FIG. 12, where br2 represents the second threshold for conditions in which the subject is not stimulated or confounded). In the event that the amount of change is not less than the first threshold and is not greater than or equal to the second threshold, blink reflex device 100 may output an indication that it is likely that the subject suffers from a neurological condition. Additionally, or alternatively, with respect to conditions in which the subject is not stimulated but is confounded, blink reflex device 100 may determine whether the amount of change in blink reflex and/or blink period (e.g., $\Delta B1$) is not less than a first threshold associated with such conditions and is not greater than or equal to a second threshold associated with such conditions (e.g., shown as $nbr1 \leq \Delta B1 < nbr2$ in some impairment field 1215 of FIG. 12, where nbr2 represents the second threshold for conditions in which the subject is not stimulated but is confounded).

Additionally, or alternatively, with respect to conditions in which the subject is stimulated and confounded, blink reflex device 100 may determine whether the amount of change in blink reflex and/or blink period (e.g., $\Delta R1$ for the right eye or $\Delta L1$ for the left eye) is not less than a first threshold associated with such conditions and is not greater than or equal to a second threshold associated with such conditions (e.g., shown as $c1 \leq \Delta R1 < c2$ in some impairment field 1215 of FIG. 12, where c2 represents the second threshold for conditions in which the subject is stimulated and confounded) (e.g., shown as $c1 \leq \Delta L1 < c2$ in some impairment field 1215 of FIG. 12). The change in blink reflex for conditions associated with other types of stimuli (e.g., light, acoustic, electrical, etc.) and confounding may be compared, in the manner described above, to other first thresholds and second thresholds for such conditions associated with the other types of stimuli and confounding.

Additionally, or alternatively, with respect to conditions in which the subject is stimulated but not confounded, blink reflex device 100 may determine whether the amount of change in blink reflex and/or blink period (e.g., $\Delta R2$ for the right eye or $\Delta L2$ for the left eye) is not less than a first threshold associated with such conditions and is not greater than or equal to a second threshold associated with such conditions (e.g., shown as $nc1 \leq \Delta R2 < nc2$ in some impairment field 1215 of FIG. 12, where nc2 represents the second threshold for conditions in which the subject is stimulated but not confounded) (e.g., shown as $nc1 \leq \Delta L2 < nc2$ in some impairment field 1215 of FIG. 12). The change in blink reflex for conditions associated with other types of stimuli (e.g., light, acoustic, electrical, etc.) but no confounding may be compared, in the manner described above, to other first thresholds and second thresholds for such conditions associated with the other types of stimuli and confounding.

Additionally, or alternatively, with respect to conditions in which the subject is stimulated and confounded, blink reflex device 100 may determine whether the amount of difference between the first blink reflex and/or blink period of the ipsilateral and contralateral eye (e.g., $\Delta LR1$) is not less than a first threshold associated with such conditions and not greater than or equal to a second threshold associated with such conditions (e.g., shown as $clr1 \leq \Delta LR1 < clr2$ in some impairment field 1215 of FIG. 12, where clr2 represents the second threshold for conditions in which the subject is stimulated and confounded). The change in the first blink reflex between the ipsilateral and contralateral eye for conditions associated with other types of stimuli (e.g., light, acoustic, electrical, etc.) and confounding may be compared, in the manner described above, to other first thresholds and/or second thresholds for such conditions associated with the other types of stimuli and confounding. Additionally, or alternatively, with respect to conditions in which the subject is stimulated but not confounded, blink reflex device 100 may determine whether the amount of difference between the first blink reflex and/or blink period of the ipsilateral and contralateral eye (e.g., $\Delta LR2$) is not less than a first threshold associated with such conditions and is not greater than or equal to a second threshold associated with such conditions (e.g., shown as $nclr1 \leq \Delta LR2 < nclr2$ in some impairment field 1215 of FIG. 12, where nclr2 represents the second threshold for conditions in which the subject is stimulated but not confounded). The change in the first blink reflex and/or blink period between the ipsilateral and contralateral eye for conditions associated with other types of stimuli (e.g., light, acoustic, electrical, etc.) and confounding may be compared, in the manner described above, to other first thresholds for such conditions associated with the other types of stimuli and confounding.

In the event that each of the amounts of change in blink reflex are not less than the respective first thresholds and are not greater than or equal to the respective second thresholds as described above, blink reflex device 100 may output an indication that it is likely that the subject suffers from a neurological condition. Additionally, or alternatively, if the difference in first blink reflex, between the ipsilateral and contralateral eye, is not less than the corresponding first threshold and is not greater than or equal to the corresponding second threshold, blink reflex device 100 may output an indication that it is likely that the subject suffers from a neurological condition.

As further shown in FIG. 10, if the change in the blink reflex is not less than the first threshold and is greater than or equal to the second threshold (block 1050—YES≥SECOND THRESHOLD), process 1000 may include outputting an indication that significant brain injury is likely (block 1065). For example, blink reflex device 100 may determine whether the amount of change in the blink reflex and/or blink period of the subject, before and after the subject experiences trauma, indicates that the subject is suffering from a significant neurological condition. Based on a determination that the subject suffers from a significant neurological condition, blink reflex device 100 may output an indication that it is likely that the subject suffers from a significant neurological condition. Such an indication may enable the user, of blink reflex device 100, to decide to prohibit the subject from resuming normal activity and/or by seeking immediate medical treatment for the subject.

For example, with respect to conditions in which the subject is not stimulated or confounded, blink reflex device 100 may determine whether the amount of change in blink reflex and/or blink period (e.g., $\Delta B0$) is greater than or equal to a second threshold (e.g., br2) associated with such conditions (e.g., shown as $br2 \leq \Delta B0$ in significant impairment field 1220 of FIG. 12). In the event that the amount of change is greater than or equal to the second threshold, blink reflex device 100 may output an indication that it is likely that the subject suffers from a significant neurological condition. Additionally, or alternatively, with respect to conditions in which the subject is not stimulated but is confounded, blink reflex device 100 may determine whether the amount of change in blink reflex and/or blink period (e.g., $\Delta B1$) is greater than or equal to a second threshold associated with such conditions (e.g., shown as $nbr2 \leq \Delta B1$ in significant impairment field 1220 of FIG. 12).

Additionally, or alternatively, with respect to conditions in which the subject is stimulated and confounded, blink reflex device 100 may determine whether the amount of change in blink reflex and/or blink period (e.g., $\Delta R1$ for the right eye or $\Delta L1$ for the left eye) is greater than or equal to a second threshold associated with such conditions (e.g., shown as $c2 \leq \Delta R1$ or $c2 \leq \Delta L1$ in significant impairment field 1220 of FIG. 12). The change in blink reflex and/or blink period for conditions associated with other types of stimuli (e.g., light, acoustic, electrical, etc.) and confounding may be compared, in the manner described above, to other second thresholds for such conditions associated with the other types of stimuli and confounding.

Additionally, or alternatively, with respect to conditions in which the subject is stimulated but not confounded, blink reflex device 100 may determine whether the amount of change in blink reflex and/or blink period (e.g., $\Delta R2$ for the right eye or $\Delta L2$ for the left eye) is greater than or equal to a second threshold associated with such conditions (e.g., shown as nc2≤ΔR2 or nc2≤ΔL2 in no impairment field 1210 of FIG. 12). The change in blink reflex and/or blink period for conditions associated with other types of stimuli (e.g., light, acoustic, electrical, etc.) but no confounding may be compared, in the manner described above, to other second thresholds for such conditions associated with the other types of stimuli and no confounding.

Additionally, or alternatively, with respect to conditions in which the subject is stimulated and confounded, blink reflex device 100 may determine whether the amount of difference between the first blink reflex and/or blink period of the ipsilateral eye and contralateral eye (e.g., ΔLR1) is greater than or equal to a second threshold associated with such conditions (e.g., shown as clr1≤ΔLR1 in significant impairment field 1220 of FIG. 12). The change in the first blink reflex and/or blink period between the ipsilateral eye and contralateral eye for conditions associated with other types of stimuli (e.g., light, acoustic, electrical, etc.) and confounding may be compared, in the manner described above, to other second thresholds for such conditions associated with the other types of stimuli and confounding. Additionally, or alternatively, with respect to conditions in which the subject is stimulated but not confounded, blink reflex device 100 may determine whether the amount of difference between the first blink reflex and/or blink period of the ipsilateral eye and contralateral eye (e.g., ΔLR2) is greater than or equal to a second threshold associated with such conditions (e.g., shown as nclr1≤ΔLR2 in significant impairment field 1220 of FIG. 12). The change in the first blink reflex and/or blink period between the ipsilateral eye and contralateral eye for conditions associated with other types of stimuli (e.g., light, acoustic, electrical, etc.) and confounding may be compared, in the manner described above, to other second thresholds for such conditions associated with the other types of stimuli and confounding.

In the event that each of the amounts of change in blink reflex and/or blink period are greater than or equal to the respective second thresholds as described above, blink reflex device 100 may output an indication that it is likely that the subject suffers from a significant neurological condition. Additionally, or alternatively, if the difference in first blink reflex, between the ipsilateral eye and contralateral eye, is greater than or equal to the corresponding second threshold, blink reflex device 100 may output an indication that it is likely that the subject suffers from a significant neurological condition.

The foregoing description provides illustration and description, but is not intended to be exhaustive or to limit the implementations to the precise form disclosed. Modifications and variations are possible in light of the above teachings or may be acquired from practice of the implementations.

While a series of blocks have been described with regard to FIG. 10, the order of the blocks may be modified in other implementations. Further, non-dependent blocks may be performed in parallel.

It will be apparent that devices and methods, as described above, may be implemented in many different forms of hardware, equipment, devices, systems, mechanical interconnections, and/or electrical interconnections in the implementations illustrated in the figures. The actual hardware, equipment, devices, systems, mechanical interconnections, and/or electrical interconnections used to implement these systems and methods is not limiting of the implementations—it being understood that hardware, equipment, devices, systems, mechanical interconnections, and/or electrical interconnections can be designed to implement the systems and methods based on the description herein. Further, certain portions, described above, may be implemented as a component that performs one or more functions.

Further, certain portions, described above, may be implemented as a component that performs one or more functions. A component, as used herein, may include hardware, such as a processor, an application specific integrated circuit (ASIC), or a field programmable gate array (FPGA), or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the implementations. In fact, many of these features may be combined in ways not specifically recited in the claims and/or disclosed in the specification. Although each dependent claim listed below may directly depend on only one other claim, the disclosure of the implementations includes each dependent claim in combination with every other claim in the claim set.

No element, act, or instruction used in the present application should be construed as critical or essential to the implementations unless explicitly described as such. Also, as used herein, the article "a" and "an" are intended to include one or more items and may be used interchangeably with "one" or "more." Where only one item is intended, the term "one" or similar language is used. Further, the phrase "based on" is intended to mean "based, at least in part, on" unless explicitly stated otherwise.

What is claimed is:

1. A method for measuring a blink of a subject, the method comprising:
   providing a blink measurement device having a sensor unit configured to measure eyelid movement of the subject;
   designating a first eyelid tracking point on an eyelid of the subject;
   tracking the first eyelid tracking point by measuring a first and second position of the first eyelid tracking point at different times;
   designating a second eyelid tracking point on an eyelid of the subject;
   tracking the second eyelid tracking point by measuring a first and second position of the second eyelid tracking point at the different times;
   defining a blink axis that intersects the first and second eyelid tracking points, wherein tracking the first and second eyelid tracking points comprises tracking movement along the blink axis;
   generating a corneal reflection along the blink axis;
   detecting a change in corneal reflection along the blink axis; and
   determining a blink of the subject based on the tracking the at least one first eyelid tracking point, tracking the second eyelid tracking point, and detecting the change in corneal reflection.

2. The method of claim 1, wherein the first eyelid tracking point is an upper eyelid tracking point.

3. The method of claim 2, wherein the second eyelid tracking point is a lower eyelid tracking point.

4. The method of claim 1, wherein tracking the first or second eyelid tracking point comprises measuring different positions at the different times.

5. The method of claim 1, wherein tracking the first or second eyelid tracking point comprises measuring the same position at the different times.

6. The method of claim 1 further comprising:
measuring and designating an initial position of the first eyelid tracking point; and
first comparing the initial position of the first eyelid tracking point with a plurality of subsequently measured positions of the first eyelid tracking point.

7. The method of claim 6 further comprising:
determining whether an eyelid is in a closing stage based on the first comparing.

8. The method of claim 6 further comprising:
determining whether an eyelid is in a closed stage based on the first comparing.

9. The method of claim 6 further comprising:
determining whether an eyelid is an on opening stage based on the first comparing.

10. The method of claim 6 further comprising:
measuring and designating an initial position of the second eyelid tracking point; and
second comparing the initial position of the second eyelid tracking point with a plurality of subsequently measured positions of the second eyelid tracking point.

11. The method of claim 10 further comprising:
determining whether an eyelid is in a closing stage based on the first and second comparing.

12. The method of claim 10 further comprising:
determining whether an eyelid is in a closed stage based on the first and second comparing.

13. The method of claim 10 further comprising:
determining whether an eyelid is in an opening stage based on the first and second comparing.

14. The method of claim 1 further comprising:
determining whether the tracking the first eyelid tracking point is greater than a first threshold, and
generating an output indicating that a condition is likely when the tracking the first eyelid tracking point is greater than the first threshold.

15. The method of claim 1 further comprising:
determining whether the tracking the first eyelid tracking point is less than a second threshold; and
generating an output indicating that a condition is unlikely when the tracking the first eyelid tracking point is less than the second threshold.

16. The method of claim 1, wherein the different times are based on a frame rate.

17. The method of claim 1, wherein the different times are based on a scan rate.

18. The method of claim 1 further comprising:
generating a blink function based on the tracking the first eyelid tracking point.

19. The method of claim 18 further comprising:
detecting an abnormal blink based on the blink function.

20. The method of claim 18 further comprising:
determining that the subject did not blink based on the blink function.

21. The method of claim 1, wherein the blink measurement device comprises a stimulator, the method further comprising:
stimulating an involuntary blink reflex.

22. The method of claim 21, wherein the stimulating comprises generating a puff of air.

23. The method of claim 21, wherein the stimulating comprises generating a puff of fluid.

24. The method of claim 21 further comprising:
determining an involuntary blink reflex reaction time based on a reflex time associated with both the stimulating and the determining a blink of the subject.

25. The method of claim 21, wherein the stimulating is at least partially deployed within a cavity of the blink measurement device.

26. The method of claim 25, wherein the cavity is configured to at least partially interface with a region of the subject's face such that the subject's eyelids can position at least partially within the cavity.

27. The method of claim 1, wherein the first eyelid tracking point is designated based on a detected corneal reflection.

28. The method of claim 1, wherein the first eyelid tracking point is designated based on a detected edge of an iris.

29. The method of claim 1, wherein the first eyelid tracking point is designated based on a detected edge of a pupil.

30. The method of claim 1, wherein the first eyelid tracking point is one of a plurality of upper eyelid tracking points.

31. The method of claim 30, wherein each of the plurality of upper eyelid tracking points is paired with a corresponding lower eyelid tracking point.

32. The method of claim 1, wherein the sensor unit comprises one or more of a camera, photodiode, electro-optical sensor, infrared sensor, ultraviolet sensor, laser diode sensor, electrode sensor, focal plan array and antenna.

* * * * *